(12) United States Patent
Rao et al.

(10) Patent No.: US 7,282,350 B2
(45) Date of Patent: *Oct. 16, 2007

(54) LABELED CELL SETS FOR USE AS FUNCTIONAL CONTROLS IN RARE CELL DETECTION ASSAYS

(75) Inventors: Galla Chandra Rao, Princeton, NJ (US); Herman Rutner, Hatboro, PA (US)

(73) Assignee: Immunivest Corporation, Wilmington, DE (US)

( * ) Notice: Subject to any disclaimer, the term of this patent is extended or adjusted under 35 U.S.C. 154(b) by 649 days.

This patent is subject to a terminal disclaimer.

(21) Appl. No.: 10/706,108

(22) Filed: Nov. 12, 2003

(65) Prior Publication Data

US 2004/0072269 A1 Apr. 15, 2004

Related U.S. Application Data

(63) Continuation-in-part of application No. 09/801,471, filed on Mar. 8, 2001, which is a continuation-in-part of application No. 09/248,388, filed on Feb. 12, 1999, now Pat. No. 6,365,362.

(60) Provisional application No. 60/074,535, filed on Feb. 12, 1998, provisional application No. 60/110,279, filed on Nov. 30, 1998, provisional application No. 60/110,202, filed on Nov. 30, 1998.

(51) Int. Cl.
*C12N 5/06* (2006.01)
*G01N 1/30* (2006.01)

(52) U.S. Cl. .................. 435/40.5; 435/40.51; 435/325

(58) Field of Classification Search ...................... None
See application file for complete search history.

(56) References Cited

U.S. PATENT DOCUMENTS

| | | | |
|---|---|---|---|
| 4,795,698 A | 1/1989 | Owen et al. |
| 5,059,518 A | 10/1991 | Kortright et al. |
| 5,187,099 A | 2/1993 | Healy et al. |
| 5,342,754 A | 8/1994 | Maples et al. |
| 5,432,089 A | 7/1995 | Ryan et al. |
| 5,529,933 A | 6/1996 | Young et al. |
| 5,597,531 A | 1/1997 | Liberti et al. |
| 5,610,022 A | 3/1997 | Battifora |
| 5,698,271 A | 12/1997 | Liberti et al. |
| 5,763,204 A | 6/1998 | Maples et al. |
| 5,888,823 A | 3/1999 | Matsumoto et al. |
| 5,968,831 A | 10/1999 | Shukla et al. |
| 5,981,282 A | 11/1999 | Ryan |
| 5,985,153 A | 11/1999 | Dolan et al. |
| 6,365,362 B1 | 4/2002 | Terstappen et al. |
| 6,551,843 B1 | 4/2003 | Rao et al. |
| 6,623,982 B1 | 9/2003 | Liberti et al. |

FOREIGN PATENT DOCUMENTS

| | | |
|---|---|---|
| EP | 91306643.7 | 12/1995 |
| JP | 63086915 | 10/1989 |
| WO | WO 98/43067 | 10/1998 |
| WO | WO 02/077604 | 10/2002 |

OTHER PUBLICATIONS

U.S. Appl. No. 09/801,471, filed Aug. 30, 2001, Terstappen et al.
L. Gomella, G. Raj & J. Moreno, "Reverse Transcriptase Polymerase . . . ," The Journal of Urology, 158:326-337 (1997), American Urological Assoc., U.S.A.
C. Stewart & J. Steinkamp, "Quantitation of Cell Concentration . . . ," Cytometry, 2(4):238-243 (1982), Wiley-Liss, Inc., New York, NY, U.S.A.
M. Keeney, J.W. Gratama, I.H. Chin-Yee & D.R. Sutherland, "Isotope Controls in the Analysis . . . ", Cytometry 34:280-283 (1998), Wiley-Liss, Inc., New York, NY, U.S.A.
G. Stelzer, G. Marti, A. Hurley, P.McCoy, E.J. Lovett & A. Schwartz, "U.S.-Canadian Consensus . . . ", Cytometry, 30:214-230 (1997), Wiley-Liss, Inc., New York, NY, U.S.A.
A. Schwartz, G.E. Marti, R. Poon, J.W. Gratama & E. Fernandez-Repollet, "Standardizing Flow Cytometry . . . ", Cytometry, 33:106-114 (1998), Wlley-Liss, Inc., New York, NY, U.S.A.
M.W. Lowdell & J. Lawry, "Quality Control in Clinical . . . ", Flow Cytometry, ed. M.G. Macey, Blackwell Scientific Publications, Oxford, U.K. (1994), pp. 45-66.
H.M. Shapiro, Practical Flow Cytometry, Wiley-Liss., New York, NY, U.S.A. (1995), pp. 302-307.
F. Hamer, "The Cyanine Dyes . . . ", The Chemistry of Heterocyclic Compounds, Interscience Publishers, New York, NY, U.S.A. (1964), pp. 86-115.
L. Terstappen, "Detection of Infrequent . . . ", Hematopoietic Stem Cell Transplantation, ed. Ho, Haaas and Champlin, Marcel Dekker, Inc., New York, NY, U.S.A. (2000), pp. 137-152.

*Primary Examiner*—Karen A. Canella
(74) *Attorney, Agent, or Firm*—Joseph F Aceto, Esq.; James L Wilcox, Esq.

(57) ABSTRACT

Methods and kits for used as an internal or external control in rare cell analysis are disclosed. A plurality of fluorescently distinct sets of cells is used to define a range to assess the isolation of rare target cells from a sample. Thus, a known number of cells, expressing the surface and intracellular antigens present in the targeted rare cells, are stabilized and modified in such a way that they can be discriminated from the targeted rare cells. In addition, these cells are separated into at least two sets based upon the number. These sets are detectably distinct from each other and provide an upper and lower indication of the detection ability of the rare cell assay.

22 Claims, 8 Drawing Sheets

Figure 1:
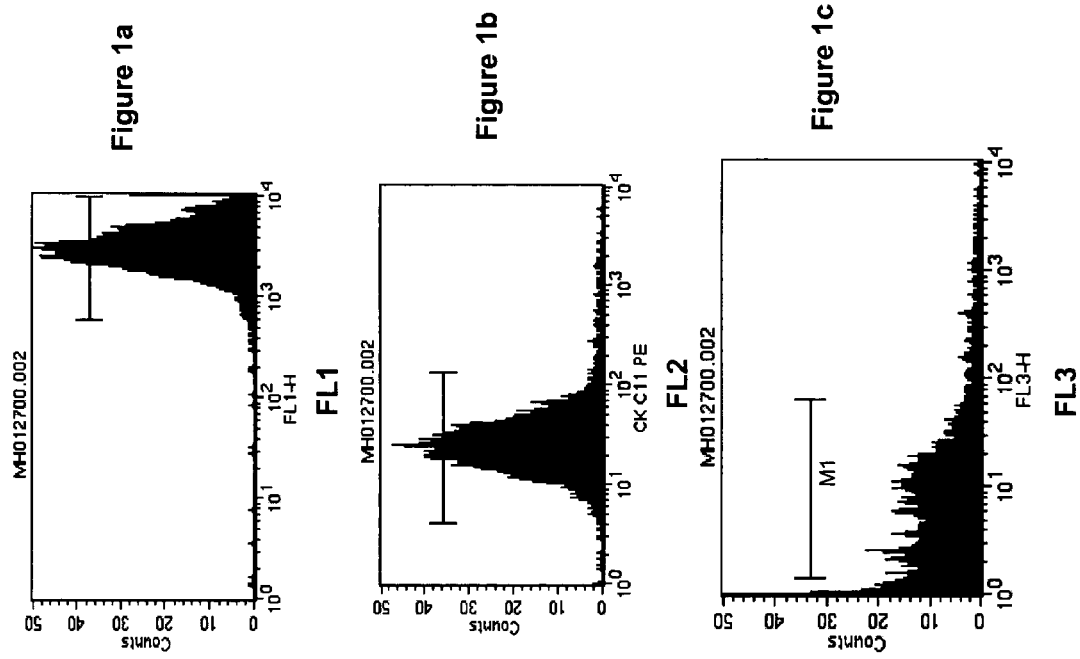

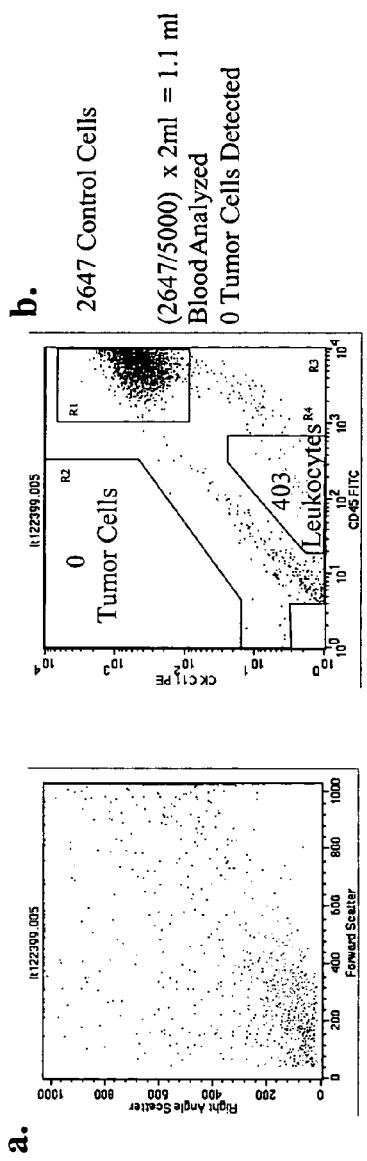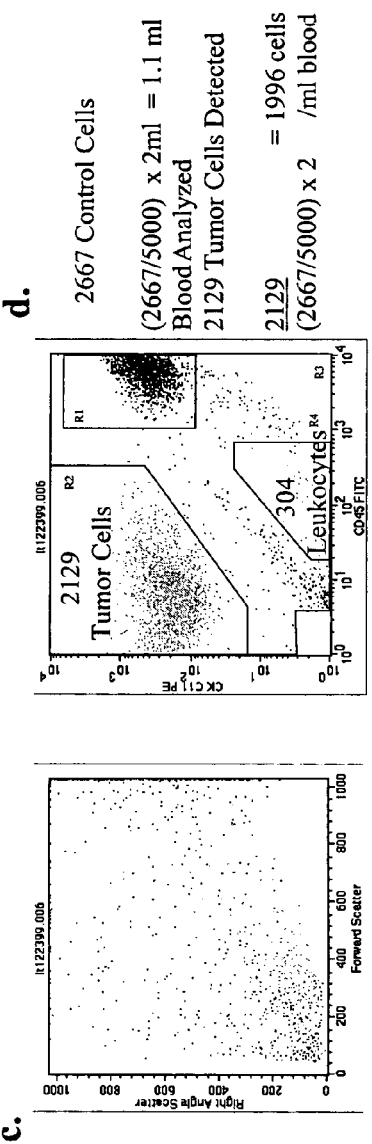
Figure 5

Figure 8
A) High Controls:
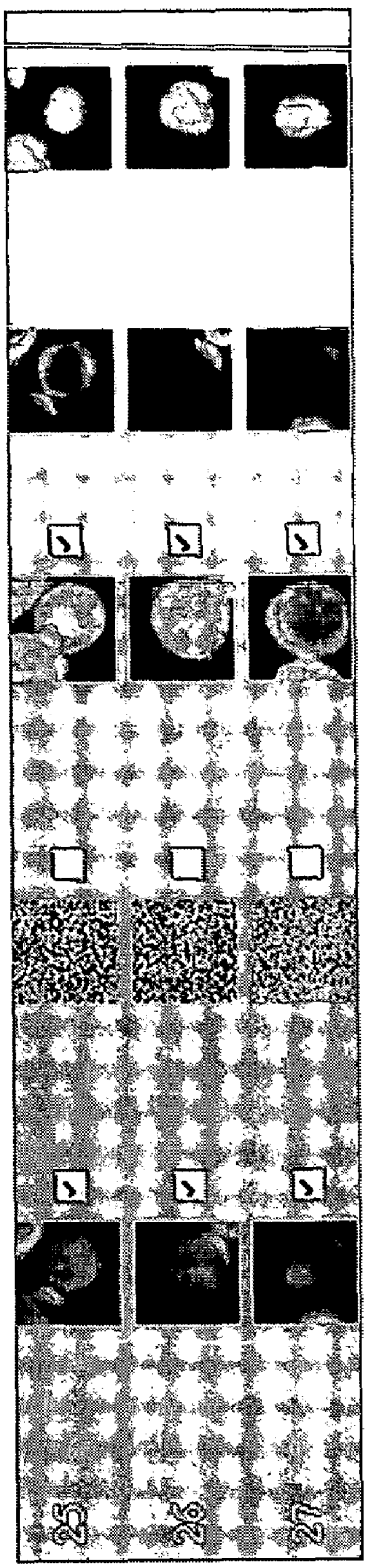
B) Low Controls:
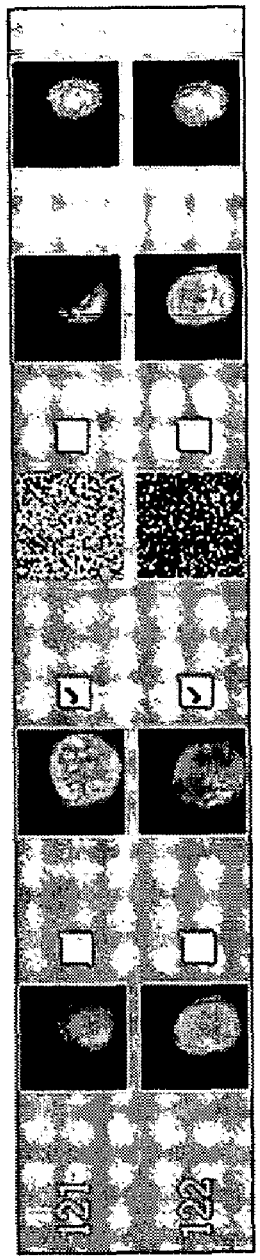

LABELED CELL SETS FOR USE AS FUNCTIONAL CONTROLS IN RARE CELL DETECTION ASSAYS

CROSS REFERENCE TO RELATED APPLICATIONS

This application is a continuation-in-part of U.S. application Ser. No. 09/801,471, filed Mar. 8, 2001, which is a continuation-in-part of U.S. application Ser. No. 09/248,388 (now U.S. Pat. No. 6,365,362), filed Feb. 12, 1999, which is a non-provisional U.S. application of U.S. Provisional Application Ser. No. 60/074,535, filed on Feb. 12, 1998, and which is a non-provisional U.S. application of U.S. application Ser. No. 60/110,279, filed on Nov. 30, 1998, and which is a non-provisional U.S. application of U.S. Provisional Application Ser. No. 60/110,202, filed on Nov. 30, 1998.

FIELD OF THE INVENTION

This invention relates to the use of pre-labeled cells as an external or internal functional control in cell selection and analysis procedures. The invention provides a range for controlling such diverse parameters as magnetic labeling, magnetic selection, viscosity, temperature, reagent addition, reagent activity, and operator error in procedures involving isolation of rare cells with the simultaneous addition of two or more fluorescently distinct sets of stabilized cells. Each set contains either a known cell number, cells with a known antigenic density, or cells of a know size. The invention is useful in aspects of cell selection, including cancer screening, staging, monitoring for chemotherapy treatments, monitoring for relapse, DNA hybridization, and numerous other forms of medical diagnosis and monitoring. The instant invention is especially useful by providing an upper and lower control in rare cell separation.

BACKGROUND OF THE INVENTION

Most cancer deaths are not caused by the primary tumor. Instead, death results from metastases, i.e., multiple widespread tumor colonies established by malignant cells that detach themselves from the site of the original tumor and travel through the body, often to distant sites. If a primary tumor is detected early enough, surgery, radiation, chemotherapy, or some combination of those treatments can often eliminate it. Unfortunately, the metastatic colonies are harder to detect and eliminate and it is often impossible to treat all of them successfully. Therefore, from a clinical point of view, metastasis can be considered the conclusive event in the natural progression of cancer. Moreover, the ability to metastasize is the property that uniquely characterizes a malignant tumor. Cancer metastasis comprises the following complex series of sequential events:
1. Extension from the primary locus into surrounding tissues;
2. Penetration into body cavities and vessels;
3. Release of tumor cells for transport through the circulatory system to distant sites;
4. Re-invasion of tissue at the site of arrest; and
5. Adaptations to the new environment so as to promote tumor cell survival, vascularization, and tumor growth.

Based on the complexity of cancer and cancer metastasis, and the frustration in treating cancer patients over the years, many attempts have been made to develop diagnostic tests to guide treatment and monitor the effects of such treatment on metastasis or relapse. Such tests presumably could also be used for cancer screening, replacing relatively crude tests such as mammography for breast tumors or digital rectal exams for prostate cancers. Towards that goal, a number of tests have been developed over the last 20 years and their benefits evaluated. One of the first attempts was the formulation of an immunoassay for carcinoembryonic antigen [CEA]. This antigen appears on fetal cells and reappears on tumor cells in certain cancers. Extensive efforts have been made to evaluate the usefulness of testing for CEA as well as many other "tumor" antigens, such as PSA, CA 15.3, CA125, PSMA, CA27.29. These efforts have proven to be somewhat futile as the appearance of such antigens in a test sample have not been generally predictive and are often detected when there is little hope for the patient. In the last few years, however, one test has proven to be useful in the early detection of cancer, viz., PSA for prostate cancers. When used with follow-up physical examination and biopsy, the PSA test has played a remarkable role in detecting prostate cancer early, at the time when it is best treated.

Despite the success of PSA testing, the test leaves much to be desired. For example, high levels of PSA do not always correlate with cancer nor do they appear to be an indication of the metastatic potential of the tumor. This may be due in part to the fact that PSA is a component of normal prostate tissue as well as other unknown factors. Moreover, it is becoming clear that a large percentage of prostate cancer patients will continue to have localized disease which is not life threatening. Based on the desire to obtain better concordance between those patients with cancers that will metastasize and those that will not, attempts have been made to determine whether prostate cells are in the circulation. When added to high PSA levels and biopsy data, the existence of circulating tumor cells might give indications as to how vigorously the patient should be treated.

The recommended approach for determining the presence of circulating prostate tumor cells has been to test for the expression of messenger RNA of PSA in blood. This is being done through the laborious procedure of isolating all of the mRNA from a blood sample and performing RT-PCR. No good correlation exists between the presence of such cells in blood and the ability to predict which patients are in need of vigorous treatment (L G Gomella, *J of Urology*, 158:326-337(1997)). It is noteworthy that PCR is difficult, if not impossible in many situations, to perform quantitatively, i.e., to determine the number of tumor cells per unit volume of biological sample. Additionally, false positives are often observed using this technique. An added drawback is the finite and practical limit to the sensitivity of this technique based on the sample size examined. Typically, the test is performed on $10^5$ to $10^6$ cells purified away from interfering red blood cells. With $5$-$10 \times 10^6$ leukocytes in normal blood, this corresponds to a practical lower limit of sensitivity of one tumor cell/0.1 ml of blood. Hence, there needs to be about 10 tumor cells in one ml of blood before signal is detectable. As a further potential complication, tumor cells are often genetically unstable. Accordingly, cancer cells having genetic rearrangements and sequence changes may be missed in a PCR assay as the requisite sequence complementarity between PCR primers and target sequences can be lost.

In summary, a useful diagnostic test needs to be highly sensitive and reliably quantitative. Such a test should be capable of detecting the presence of a single tumor cell in one ml of blood, thus corresponding on average, to 3000-4000 total cells in circulation. In inoculum studies for establishing tumors in animals that number of cells can indeed lead to the establishment of a tumor. Further, if 3000-4000 circulating cells represent 0.01% of the total cells in a tumor, then it would contain about $4\times10^7$ total cells. A tumor containing that number of cells would not be visible by any technique currently in existence. Hence, if tumor cells were shed in the early stages of cancer, a test with the sensitivity mentioned above would detect the cancer. If tumor cells were shed in some functional relationship with tumor size, then a quantitative test would be beneficial to assessing tumor burden. Heretofore, there has been no information reported regarding the existence of circulating tumor cells in very early cancers. Further, there are very considerable doubts in the medical literature regarding the existence of such cells and the potential of such information. The general view is that tumors are initially well confined and hence there will be few if any circulating cells in early stages of disease, and that early detection of cancer cells in circulation, even if feasible, would be unlikely to yield any useful information.

Based on the above, it is apparent that a method for identifying those cells in circulation with metastatic potential prior to establishment of a secondary tumor is highly desirable, particularly during the early stages of cancer. To appreciate the advantage such a test would have over conventional immunoassays, consider that a highly sensitive immunoassay has a lower limit of functional sensitivity of $10^{-17}$ moles. If one tumor cell can be captured from one ml of blood and analyzed, the number of moles of surface receptor, assuming 100,000 receptors per cell would be 10-19 moles. Since about 300 molecules can be detected on a cell, such an assay would have a functional sensitivity on the order of $10^{-22}$ moles, which is quite remarkable. To achieve that level of sensitivity in the isolation of such rare cells and to isolate them in a fashion which does not compromise or interfere with their characterization is a formidable task.

The introduction of flow cytometry to discriminate between cell populations has significantly improved the ability to accurately identify and enumerate components of cell populations that cannot be distinguished by morphological features. A further improvement of the sensitivity of flow cytometric examination of heterogeneous cell mixtures has been obtained by multidimensional analysis of the data. Cell populations are identified by the simultaneous assessment of light scattering and fluorescence parameters. Light scattering parameters measure cell size and cell granularity. Fluorescence parameters can be used to assess cell surface antigens, intracellular antigens, DNA, RNA, and protein content. By simultaneous analysis of light scatter and fluorescence parameters of individual cells passing through the laser beam, a multidimensional space is created in which the cells with dissimilar properties emerge in different locations. Conditions needed to detect infrequent/rare cells by flow cytometry are:

1. Sufficient sample volume for analysis;
2. Analysis by flow cytometry in a reasonable amount of time;
3. Selection of parameters such that the cell population of interest is located in a unique position;
4. Frequency of the target cells should be higher then 1 in $10^5$ cells.

The current sample preparation procedures in which blood samples are incubated with fluorescently-labeled antibodies followed by addition of an erythrocyte lysing agent dilutes the sample ten-fold and is thus not suitable for detection of rare cells. In research laboratories, density separations or erythrocyte lysing procedures achieve reduction of the sample volume and an increase in cell concentration. These procedures lead to variable cell losses and are difficult to standardize between laboratories. Moreover, no significant enrichment of the target cells is obtained.

One method for isolating circulating tumor cells for analysis and enumeration is described in U.S. Pat. No. 6,365,362. The method described therein uses a magnetic particle labeled with antibodies to markers commonly found on circulating tumor cells that can be magnetically selected from a patient blood sample. Assays based on this method have shown not only that breast cancer tumor cells can be found in the blood of a patient with tumors at the lower limit of detection by mammography, but that the number of circulating tumor cells can be correlated to conventional therapies. For example, the number of circulating tumor cells decreases with chemotherapeutic treatments or surgery. Other tests using this method have shown that the number of circulating tumor cells is proportional to the tumor mass in several patients with colon cancer. Still, other tests showed that as a cancer patient comes out of remission, the number of circulating tumor cells increases. These remarkable results were found in a variety of cancers, including cancers of the breast, prostate, and colon.

As exciting as these results are, they must be tempered with the proper amount of scientific restraint. While the detection of circulating tumor cells in one's blood is frightening to the patient, a negative test result has not yet been proved to be an indication that a patient is free of cancer. Even worse would be a false-negative result for circulating blood cells. Reagent failure, instrument failure and operator errors can all lead to erroneous negative results. As the cancer cells in blood are rare, (often less than 1 cell/ml of blood) the blood volumes needed to perform the test are restrictively large. The requirement for such a large volume of blood prohibits the use of additional blood samples for traditional external control purposes. As discussed by Terstappen in "Detection of infrequent cells in blood and bone marrow by flowcytometry", Hematopoietic Stem Cell Therapy, ed. A. Ho, Marcel Dekker Inc. pp. 137-152, (2000) to test non-specific (negative) binding in non-rare, traditional cell detection assays, the number of cells counted is generally less than 1% of the starting cell population. In the actual test, the specific reagents detect a cell population generally larger than 1%, thus confirming that the reagents are actually working. This non-specific binding (NSB) would result in a cell count of $10^5$ cells, if one started with $10^7$ cells and a NSB of 1%. However, in cancer cell detection, the specific binding of 0 cells may be detected in a cancer-free patient and must be discriminated from the presence of 1-100 circulating tumor cells in a patient who is undergoing relapse. With 0 cells detected, one has no way of knowing whether the reagents and/or process are working. An internal/indwelling control for assessing each of the components used in the test is thus desirable.

In order to have the required certainty that a test result is valid, controls at a number of essential points in the process are necessary. The first essential point that needs control is the magnetic labeling step. With so few tumor cells in the test sample, it is vital that these cells be targeted by the antibody-bearing magnetic particles. Another point is the magnetic selection of the magnetically labeled targets, which includes aspirating the excess liquid and non-selected cells, and the further washing of the magnetic particle/cell complexes. Still another point in the procedure is the step of labeling with antigen specific fluorescent dyes, some of which target antigen present on the cellular surface, but some of which require the permeabilization of the cellular and/or nuclear membrane. Yet another point is the enumeration of the actual target cells. As described in U.S. Pat. No. 6,365,362, enumeration is performed by flow cytometry, but use of the system described in U.S. Pat. No. 6,623,983 or the system described in U.S. Pat. No. 5,985,153 may also be employed if desired. These patents are incorporated by references herein.

One example of an experimental control is the use of 'isotopic dilution' to determine yield in chemical reactions or purifications. In this procedure, a pure sample of the molecule or compound of interest is labeled with a radioactive isotope of one of the atoms in the molecule. A known amount of the isotopically labeled compound is added to starting material and the chemical reaction or isolation procedure is run. At the end of the process, the percentage of isotopically labeled compound is calculated. The comparison between the original starting materials and the final product allows a calculation of the yield or percentage recovery of the starting material. This type of control also allows for sophisticated analysis of which steps in a process result in the loss of product or low yields. Use of a genuine 'isotopic dilution' protocol is not possible in the isolation of biological materials, such as cells, especially tumor cells. However, the use of cells which are labeled with a characteristic marker to distinguish them from the target cells, and which behave in a manner which could be proven to be very similar to the target cells would be useful to impart some information about percentage recovery to the researcher.

The traditional controls for immunophenotyping of cells are isotype controls. In an isotype control, the test is run using a monoclonal antibody of the same isotype, same species, but directed against an irrelevant antigen. In the circulating tumor cell assay mentioned above, the monoclonal antibody on the magnetic particle is directed against the epithelial cell adhesion molecule (EpCAM). The clone used in the examples in this specification is a mouse antibody IgG1κ. The traditional isotype control for this particle should be a magnetic particle prepared identically, only now the particle is labeled with a mouse antibody IgG1κ, directed against an antigen that does not appear in humans, such as keyhole limpet hemocyanin (KLH). Cells selected after magnetic separation with this isotype antibody on the magnetic particle are non-specifically bound, and the number of non-specifically selected cells can be determined. The IgG1κ monoclonal antibody directed against the leukocyte antigen CD45 is labeled with fluorescein isothiocyanate (FITC). The traditional isotype control is a FITC-labeled monoclonal IgG1κ antibody directed against an antigen which is not expressed in humans, such as KLH. Cells selected after magnetic separation and stained with this FITC-labeled isotype antibody determine the background staining in the FITC channel. The monoclonal antibody directed against the cytokeratins 4, 5, 6, 8, 10, 13, and 18 is labeled with phycoerythin (PE). This antibody is a murine monoclonal antibody, IgG1κ. The traditional isotype control is a PE-labeled monoclonal IgG1κ antibody directed against an antigen that does not appear in humans, such as KLH. Cells selected after magnetic separation and stained with this PE-labeled isotype antibody determine the background staining in the PE channel. Thus, all the antibodies in the system would be identical to those in the patient sample, except for the specificity. Cell selection with these reagents would be run side-by-side with a patient sample, using an identical aliquot of patient blood. If multi-parameter flow cytometry were used for the final analysis, the results would show a population of cells and the gates for the detection of tumor cells [FITC−, PE+] can be selected.

To discriminate between the non-specifically staining cells and the non-specifically selected cells, an additional blood sample, free of tumor cells, would be run using the isotype control magnetic particle, the CD45-FITC and the isotype control PE. If multi-parameter flow cytometry were used, the FITC[+] cells would be the non-specifically selected leukocytes. The FITC[+], PE[+] cells would be the non-specifically selected and the non-specifically staining cells. Cells that are FITC[−], PE[+] would be non-specifically selected cells that were binding non-specifically to PE, but not to the FITC MAb, as the isotype of both antibodies is the same. This non-specific binding is due to the fluorochrome, and not the antibody, or changes caused by the conjugation. Roughly, the same number of leukocytes would also appear in the patient sample with specific reagents, which also would have been non-specifically selected, yet specifically stained. Differential analysis effectively removes these leukocytes from the test results, offering further assurance that any "tumor cells" detected in the test are actually circulating epithelial cells and not non-specifically bound blood cells.

A more accurate control would be to use the EpCAM FF, the CD45-FITC, and an isotype PE MAb. In a patient sample, the majority of the selected cells are non-specifically selected. These cells are recognized by the CD45-FITC MAb and can thus be enumerated and they represent the true non-specific selection by the EpCAM FF. The actual tumor cells will not be stained with CD45-FITC, nor with the isotype control PE antibody. However, as the frequency is extremely low, one cannot determine whether there are actually tumor cells in the patient sample.

Although the traditional isotype controls described above represent the types of controls appropriate to cell selection, they are not truly functional controls. First, the level of background varies considerably, depending on which antibody is chosen for an isotype control. Thus, the choice of isotype controls could be made to influence a higher or lower background threshold. Second, this type of control does not account for the reagents used in the actual patient test. For example, the anti-cytokeratin antibody in the patient test may have been inadvertently omitted from the test mixture. This mistake would be undetected by the isotype control. Finally, and most importantly, this type of isotype control can be used for small blood samples, which require 50-150 μl of blood. However, in rare cell isolation, a full tube, and optimally 5-30 ml of whole blood is required for the detection of tumor cells. Cell numbers as low as 1 cell/ml of blood have been detected, thus the larger the sample, the less likely the test will miss a patient with a low incidence of circulating tumor cells. These cancer patients are already subjected to a variety of medical tests, so the draining of an extra 20-30 ml of blood for an isotype control of limited value is not acceptable. Use of a small blood sample for an isotype control is also of limited value. Dividing the blood sample into an isotype control and the actual test sample decreases sensitivity, and those patients with a low level of circulating tumor cells would be missed. As documented by Stelzer, et al, Cytometry 30:214-230 (1997) and Keeney, et al, Cytometry 34:280-283 (1998), consensus is building towards elimination of a patient sample for use as any type of control, including an isotype control.

Immunicon's U.S. Pat. No. 5,985,153 describes an internal control, which is substantially different from an external, isotype control. In Examples 6 and 7 of the '153 patent, beads with a magnetic "load" or antigen "loads" similar to those found on cancer cells are added to the blood sample. The percentage or number of beads detected by the test is used to determine the efficiency of the test. The use of beads as a control is well known in the art and has a clear advantage as there is no chance of mistaking a bead for a cell during the analysis of the test. Beads also store well and can be reproducibly manufactured, and have the added benefit that they can be used to accurately determine the volume of a sample. As described by Stewart et al, Cytometry 2(4): 238-243 (1982), the use of a known quantity of fluorescent beads overcomes the common problem of determining the sample volume actually analyzed by a flow cytometer. However, the use of beads as a control has limitations. Beads can be extremely sturdy, and as such unaffected by numerous conditions that would destroy a cell, thus limiting their usefulness as a control against operator error. Sensitivity of the bead to conditions such as temperature, pH, and isotonic strength should be similar to that of an actual cell. The engineering and manufacturing considerations for forming such a bead with the appropriate antigens, antigen density, and dyes to provide a control for the cell selection would be difficult. Not only must the bead have the appropriate antigens, they must be accessible under conditions similar to that of an actual cell. For example, steric factors and binding constants must be taken into consideration. Finally, beads are solid objects, not affected by the permeabilization reactions, limiting their usefulness as a control at that crucial step. Therefore, even if one could perfectly duplicate a cell surface, beads could still not serve as a true internal, positive control for a cell selection test.

Another approach to providing a control would be to use actual cells as controls. Indeed, a standard quality control procedure for cell surface phenotyping is to obtain specimens from normal donors to be prepared and analyzed concomitantly with the patient's sample. Ideally, the normal specimen is of the same type, and obtained at the same time, as the patient sample, although this is generally not possible for specimens other than peripheral blood. Even with peripheral blood, the use of fresh blood can be costly, time-consuming, and not always available, causing many labs to turn to stored cell products as the source of their controls. The use of prepared, commercially obtained, preserved cells as controls for various medical tests are well known in the art. Control cells embedded in gelatin, paraffin, or agar are described in U.S. Pat. No. 5,610,022 (Battifora) and U.S. Pat. No. 5,187,099 (Healy, et al.). The use of preserved cells for reference controls for cell counters are described in U.S. Pat. No. 5,981,282 (Ryan); U.S. Pat. No. 5,432,089 (Ryan); U.S. Pat. No. 5,342,754 (Maples, et al); and U.S. Pat. No. 5,763,204 (Maples, et al.). Preservation by lyophilization is also used, as described in U.S. Pat. No. 5,059,518 (Kortright, et al.); U.S. Pat. No. 5,968,831 (Shukla, et al.); and European patent 469 766B1 (Davis). The creation of a standard solutions used for cells counters, flow cytometers and other instruments are described in U.S. Pat. No. 5,529,933 (Young, et al.); U.S. Pat. No. 5,888,823 (Matsumoto, et al.); and Japanese accepted specification 01259261. A review of the catalogs of the major suppliers of reagents for hematology analyzers, flow cytometers, and other cell analysis platforms reveals a large number of cell-based controls for these instruments. Some examples include Streck Laboratories Cell-Chex® and Chem-Chex reagents, R&D Systems R&D Retic reagents, Beckman-Coulter Cyto-Trol® control cells, and BioErgonomics FluoroTrol® line of stabilized leukocytes.

Although the control cells described in the above-mentioned patents and the various commercially available reagent lines offer many forms of stabilized cells for cell procedures, the methods and reagents described would only be able to provide external controls for cell selection and analysis procedure. None would provide a suitable internal control for the selection and enumeration of rare cells, such as circulating tumor cells. In addition, the stability of the cells is limited to 14-30 days. In those cases where there is longer stability, the cells have been lyophilized, which increases shelf life, but may decrease reproducibility, due to inadequate reconstitution.

If one were to use cells as an external or internal, positive control for rare cell selection, many problems are presented. For example, how are the cells obtained? How can the control cells be differentiated from the target cells? How can one prove that the control cells behave similar to the target cells? How can the cells be used to control the experiment? Is the recognition ability similar across all levels of target cell detection? Use, reproducibility, and efficacy are essential concerns regarding the use of cells as an external or internal positive control for cell selection, all of which are addressed in the present invention.

SUMMARY OF THE INVENTION

In a procedure to isolate rare target cells from a sample that also comprises non-target cells, a reproducible, standardized internal control system is required. Therefore, a known number of cells, that express surface and intracellular antigens that are present in the targeted rare cells, are stabilized and modified in such a way that they can be clearly discriminated from the targeted rare cells. These "control cells" are added directly to a patient's whole blood sample before the sample is processed. The number of the control cells detected after the patient sample is analyzed and the fluorescent characteristics of the control cells as determined via the analytical platform to confirm that the reagents are working properly and indicate that the patient sample has been processed accurately.

At present, the breast cancer cell line SKBR-3 has been successfully stabilized for use as control cells. The cells may be fluorescently labeled with the lipophyllic membrane dye, 3,3'-dihexadecycloxacarbocyanine perchlorate ($DiOC_{16}(3)$), ($DiOC_{18}(5)$), or other dyes and labels such that the control cells can be clearly discriminated from a "true" tumor cell. These SKBR-3 cells have certain features that enhance their use as control cells in the selection of tumor cells, including:

1. They express the epithelial cell adhesion molecule (EpCAM) antigen and are selected from blood by magnetic particles coated with EpCAM MAb;

2. The membranes of the control cells are permeabilized by the permeabilization reagent;

3. The control cells express intracellular cytokeratins and are identified by a fluorescently labeled anticytokeratin MAb;

4. The control cells do not express CD45 antigen and should not stain with the fluorescently labeled anti-CD45 antibody; and 5. The control cells have a nucleus and should stain with a fluorescent compound staining the nucleus.

The recovery of the control cells accurately reflects the recovery of circulating tumor cells in patient samples. Although it impossible to prove that control cells behave exactly like a circulating epithelial tumor cell, it can be shown in that, using the magnetic separation technique described, no significant difference in recovery of cultured tumor cells were found, whether or not they had a high or low antigen density. The antigen density range of cell lines available is similar to the range of tumor cells found in cancer patients.

While there may be similarity in the range of antigen density of most tumor cells, this assumption is not definite across all cell lines and, in fact, may vary during different stages of the disease, especially when not using a controlled aggregation (U.S. Pat. Nos. 6,623,982 and 6,620,627). Further, there may be alternative considerations, separate from controlling for the assay, to make the use of an internal control undesirable. Thus, external or internal control cells can be used to provide a range for comparison of the available cell line, used as a control, and the tumor cell found in cancer patients.

In one aspect of the invention, stabilized cells for use as either internal or external controls in methods for isolating and identifying rare cells are provided. The control cells of the invention have determinants in common with rare cells, and are membrane labeled. The cellular components and antigenic moieties of the control cell have been stabilized for a period up to six months by exposure to fixative. In a preferred embodiment, the cellular components and antigenic moieties, present in the control cell, are shared by the targeted rare cell. Two or more fluorescently distinct sets of control cells are used, providing an upper and lower population of cell numbers. Sets of control cells are distinguished by fluorescent characteristics such as, but not limited to, spectral emission/absorption profile or intensity. Optionally, the cells within each set may be redundantly membrane labeled, having at least two further distinct fluorescent labels as described in U.S. patent application Ser. No. 09/801,471.

Also in accordance with the present invention are improved methods for isolating and enumerating rare cells, increasing numbers of rare cells being indicative of a disease state. In a particularly preferred embodiment, the rare cell is a cancer cell and the disease state is cancer. An exemplary method of the invention includes the following steps: i) obtaining a blood sample from a test subject, the sample comprising a mixed cell population suspected of containing said rare cells; ii) preparing an immunomagnetic sample wherein the blood sample is mixed with magnetic particles coupled to a ligand which reacts specifically with a determinant of the rare cells, to the substantial exclusion of other sample components; iii) contacting the immunomagnetic sample with at least one reagent which labels a determinant of the rare cells; and iv) analyzing the labeled rare cells to determine the presence and number of any rare cells in the immunomagnetic sample, the greater the number of rare cells present in said sample, the greater the severity of the disease state, the improvement comprising the addition of two fluorescently distinct sets of stabilized cell populations for use as internal or external control cells in said method, wherein the membrane of said control cell is detectably labeled and cellular components and antigenic moieties of the control cell have been stabilized for a period up to six months by exposure to fixative. In one embodiment of the aforementioned, the ligand is an anti-EpCam antibody and the reagent specifically binds a cytokeratin.

In an additional embodiment of the present invention, a kit is provided which facilitates the practice of the methods described herein. An exemplary kit for isolating circulating epithelial (tumor) cells in human blood includes: coated magnetic nanoparticles comprised of magnetic core material, a protein base coating material, and an antibody that binds specifically to epithelial-derived cells, the antibody being coupled, directly or indirectly, to said base coating material; at least one antibody having binding specificity to the epithelial derived tumor cells, which is labeled with a detectable label; and two fluorescently distinct sets of stabilized control cell populations that are labeled with a detectable label and which bear at least one surface antigen in common with the rare cells of interest. The kit may optionally contain permeabilizing reagents, wash and/or dilution buffers, aggregation reagents, additional detectably labeled antibodies or additional cell specific dyes.

A BRIEF DESCRIPTION OF THE DRAWINGS

FIGS. 1A to C: Flow cytometric analysis of control cells.

Figure 2:
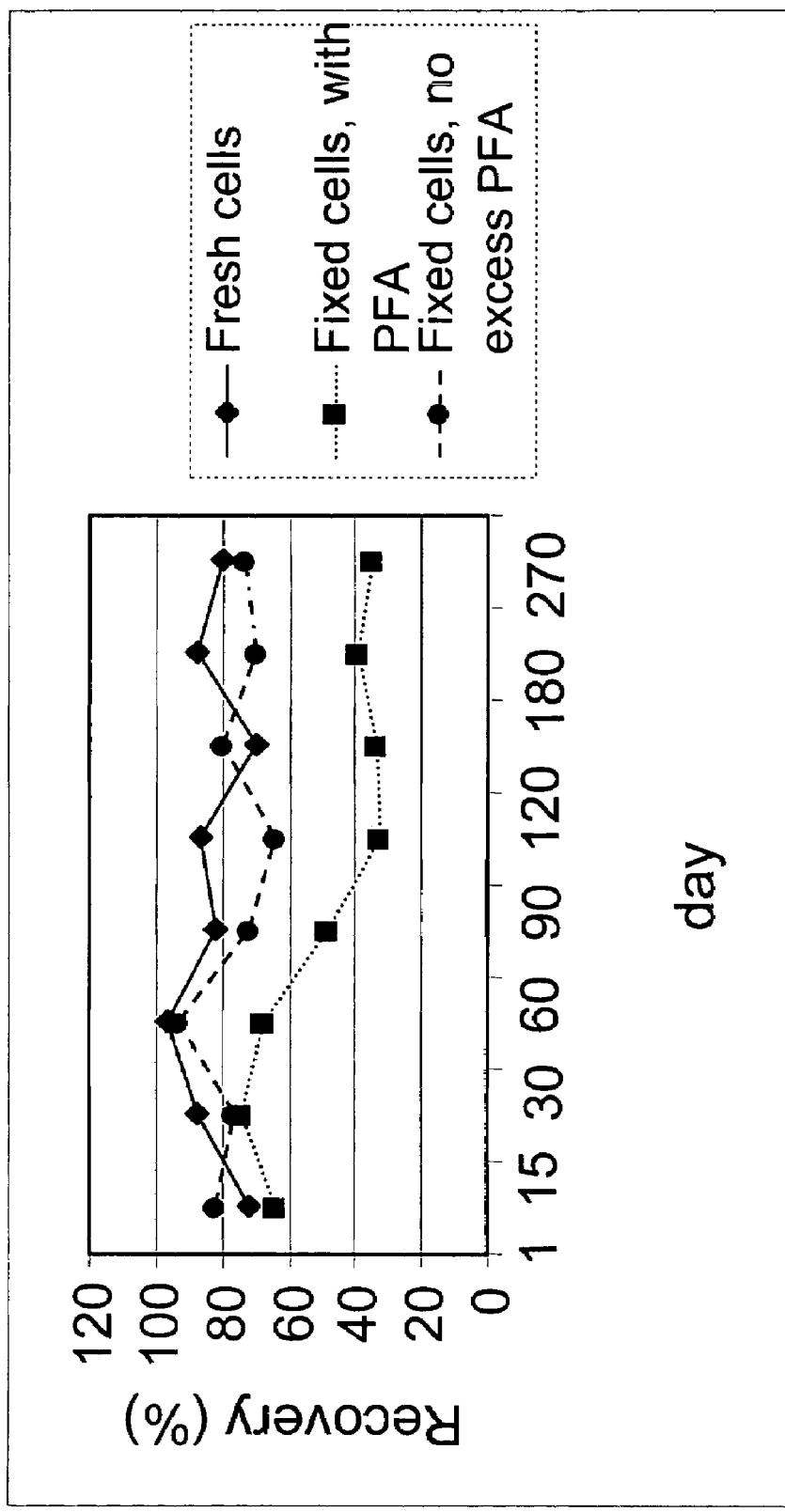

FIG. 2: Stability of fixed SKBR-3 cells (pre-labeled with HER2neu-Cy2™ MAb) in excess paraformaldehyde (PFA) or no PFA, compared to fresh cells.

Figure 3:
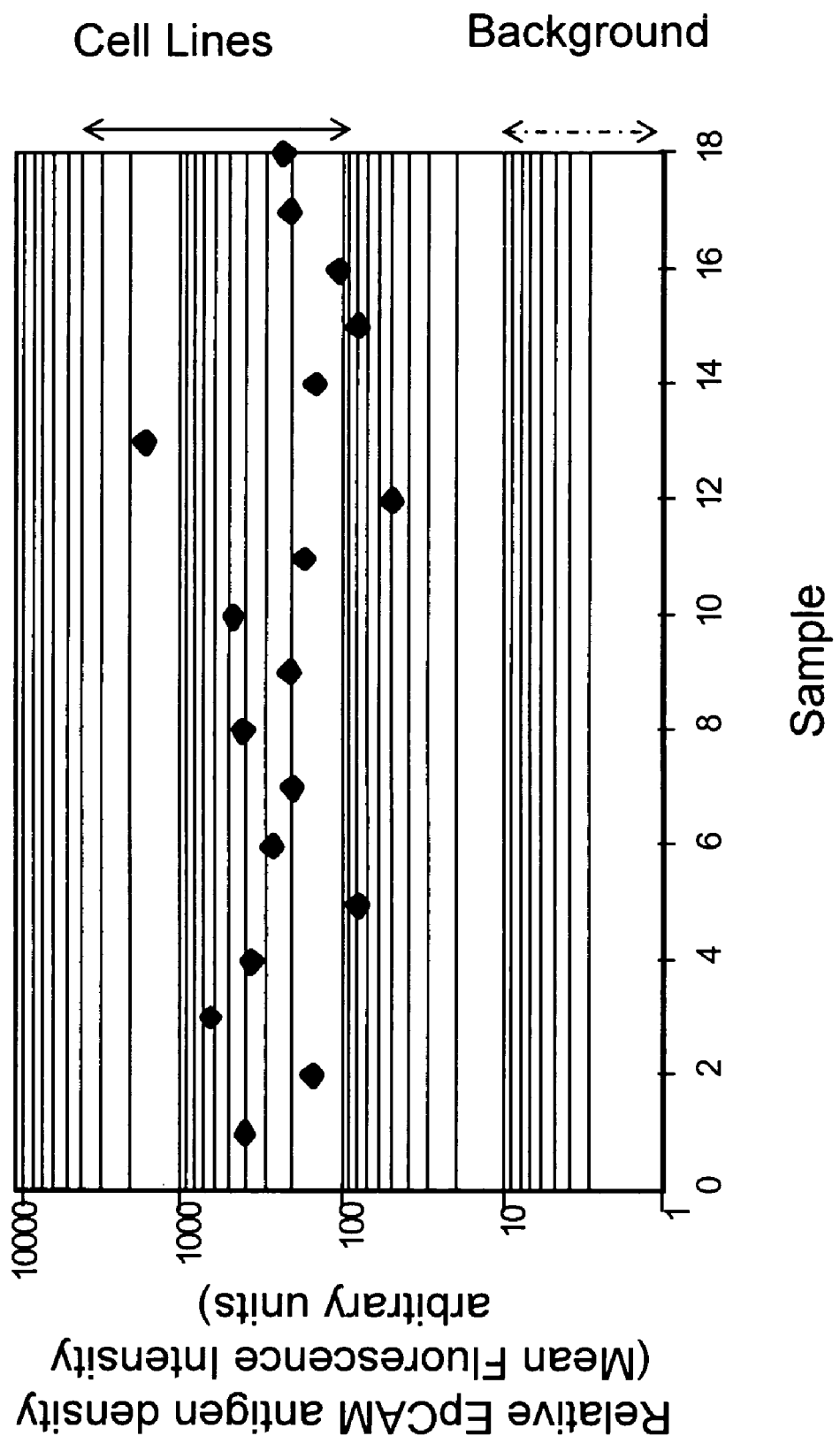

FIG. 3: Antigen density, as measured by mean fluorescence intensity in 18 patients with breast cancer.

FIGS. 4a to e: Cell Spotter® analysis of EpCAM ferrofluid selected cells from a prostate cancer patient's blood.

FIGS. 5a to d: Flow cytometric analysis of EpCAM ferrofluid selected cells from blood, with and without a tumor cell spike.

FIGS. 6a to d: Flow cytometric analysis of EpCAM ferrofluid selected cells from blood, without a tumor cell spike.

FIGS. 7a to d: Flow cytometric analysis of EpCAM ferrofluid selected cells from blood, spiked with tumor cells.

FIGS. 8a and b: Browser images showing the fluorescent images of the high and low controls.

DETAILED DESCRIPTION OF THE INVENTION

I. General Definitions

Unless otherwise indicated, terms of general usage throughout the present specification are defined as follows.

The term "target bioentities" as used herein refers to a variety of materials of biological or medical interest. Examples include hormones, proteins, peptides, lectins, oligonucleotides, drugs, chemical substances, nucleic acid molecules, (e.g., RNA and/or DNA) and particulate analytes of biological origin, which include bioparticles such as cells, viruses, bacteria and the like.

The term "rare cells" as used herein refers to a variety of cells, microorganisms, bacteria, and the like. Cells are characterized as rare in a sample because they are 1) not present in normal samples of the same origin, and 2) are several orders of magnitude lower in concentration than the typical cells in a normal sample. In a preferred embodiment of the invention, circulating cancer cells, virally infected cells, or fetal cells in maternal circulation may be efficiently isolated from non-target cells and/or other bioentities, using the compositions, methods, and kits of the present invention.

The term "biological specimen" includes, without limitation, cell-containing bodily fluids, peripheral blood, bone marrow aspirates, bone marrow biopsies, lymphoid tissue biopsies, tissue homogenates, fine needle aspirates, serosal fluids, spinal fluids, skin, mucosa, nipple aspirates, and any other source of cells that is obtainable from a human subject. An exemplary tissue homogenate may be obtained from the sentinel node in a breast cancer patient. Biological specimens may also be obtained from treated water samples and food products.

The term "determinant", when used in reference to any of the foregoing target bioentities, may be specifically bound by a biospecific ligand or a biospecific reagent, and refers to that portion of the target bioentity involved in, and responsible for, selective binding to a specific binding substance, the presence of which is required for selective binding to occur. In fundamental terms, determinants are molecular contact regions on target bioentities that are recognized by receptors in specific binding pair reactions.

The term "specific binding pair" as used herein refers to any substance that selectively recognizes and interacts with a determinant on a target bioentity. Specific binding pairs include antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin and virus-receptor interactions. Various other determinant-specific binding substance combinations are contemplated for use in practicing the methods of this invention, such as will be apparent to those skilled in the art. The term "antibody" as used herein, includes immunoglobulins, monoclonal or polyclonal antibodies, immunoreactive immunoglobulin fragments, and single chain antibodies. Also contemplated for use in the invention are peptides, oligonucleotides or a combination thereof which specifically recognize determinants with specificity similar to traditionally generated antibodies.

The term "detectable label" is used to herein to refer to any substance whose detection or measurement, either directly or indirectly, by physical or chemical means, is indicative of the presence of the target bioentity in a test sample. Dectably prelabeled control cells of the present invention bear epitopes common with target cells, but are differentially detected from the same target cells. Representative examples of useful detectable labels include, but are not limited to molecules or ions directly or indirectly detectable based on light absorbance, fluorescence, reflectivity, light scatter, phosphorescence, or luminescence properties; molecules or ions detectable by their radioactive properties; molecules or ions detectable by their nuclear magnetic resonance or paramagnetic properties. Included among these molecules are those which can be indirectly detectable based on light absorbance or fluorescence, for example, various enzymes which cause appropriate substrates to convert, e.g., from non-light absorbing to light absorbing molecules, or from non-fluorescent to fluorescent molecules.

The term, "cell specific dyes" describes a free or unconjugated dye, which stains a specific cellular element (e.g. nuclear stains differentiating DNA and RNA), or a dye conjugated to a binder, which selectively binds to and stains a specific cellular receptor.

The phrase "to the substantial exclusion of" refers to the specificity of the binding reaction between the biospecific ligand or biospecific reagent and its corresponding target determinant. Biospecific ligands and reagents have specific binding activity for their target determinant yet may also exhibit a low level of non-specific binding to other sample components.

The term "early stage cancer" as used herein refers to those cancers that have been clinically determined to be organ-confined. Also included are tumors too small to be detected by conventional methods, such as mammography for breast cancer patients, or X-rays for lung cancer patients. While mammography can detect tumors having approximately $2 \times 10^8$ cells, the methods of the present invention should enable detection of circulating cancer cells from tumors approximating this size or smaller.

The term "enrichment" as used herein refers to increasing the ratio of the target cells to total cells in a biological sample. In cases where peripheral blood is used as the starting materials, red cells are not counted when assessing the extent of enrichment. Using the method of the present invention, circulating epithelial cells may be enriched relative to leukocytes to the extent of at least 2,500 fold, more preferably 5,000 fold, and most preferably 10,000 fold.

The term "assay" as used herein refers to a procedure or a series of procedures using known reagents for the purpose of determining the absence or presence of a target bioentity in a biological specimen. An assay may include quantitated reagents and established protocols to assess the presence, absence, or activity of a biological entity.

The term "test system" is used herein to signify the entire procedure using known reagents for determining the absence or presence of a target bioentity in a biological specimen. The test is performed by an operator with the system that includes at least one assay, the hardware and software (if any) used to perform the assay(s), and the analysis of the results of the assay(s).

The term "standard" is used herein to signify materials which are used to set up and/or calibrate an instrument and which do not require additional preparation. In addition, standards have specific properties similar to the analyte, e.g., a microbead population having a specific intensity and wavelength to set the analysis range of an instrument and/or quantify fluorescence intensity.

The term "control" describes a substance or mixture of known composition with properties that fall within pre-determined ranges and is designed to undergo the same processing protocols as the analyte or substance of interest to ensure that reagents and/or cell preparations are working as expected.

The term "isotype control" refers to the use of a monoclonal antibody of the same isotype, same species, but directed against an irrelevant antigen. Isotype controls are widely used to set the discriminatory level between non-specific background and positive fluorescent staining.

The term "external control" as used herein refers to any substance or mixture of known composition that is subjected to the same conditions as the test substance within an assay or a test system, but external to the actual test sample, for the purpose of establishing a basis for comparison with the test substance. Thus, an external control allows for detection of systemic errors but not random errors. An external control may be a positive or a negative control and multiple external controls may be used within one test system.

The term "internal control" refers to any substance or mixture of known composition that is added to or mixed with a test substance within a test system for establishing a basis for comparison with the test substance. By virtue of the simultaneous presence of the test substance and the control substance, the two substances undergo identical conditions within the test system, providing an explicit measure of the efficacy of the entire test system. An internal control detects both systematic and random errors and is preferred over external controls, but only if the added internal control can be unequivocally differentiated from the test substance. In a preferred embodiment of the invention, a quantified and appropriately labeled functional control cell aliquot added to a patient blood sample provides not only an internal control of the test system, but also a quantifiable and analytical control of cell recovery in the test system. In other words, based on the recovery of control cells at the end of the analysis, it is possible to consider not only how many target cells were actually retrieved, but also what volume of sample was actually processed. This allows a more accurate prediction of the range of tumor cell incidence in the patient sample.

The term "two-fluorescently distinct sets" as used herein refers to separate populations of an internal or external control added to or mixed with a test substance within a test system for establishing a basis for comparison with the test substance. Populations are based upon the cell number, antigen density per cell, or individual cell size.

The term "negative control" as used herein refers to an internal or external control substance that behaves in a manner generally similar to the target bioentity. However, the negative control substance lacks at least one of the characteristic determinants that distinguish the target bioentity from other biological entities, such that at the end of the assay or the test procedure, the negative control substance is not detected.

The term "positive control" refers to an internal or external control substance which behaves in a manner similar to the target bioentity, and includes the characteristic determinants which are used in the assay or test procedure to distinguish the target bioentity from other biological entities. In fact, in some cases a positive control actually functions as the target bioentity. A positive control put through an assay or a test system is present at the end of the assay or the test procedure, thus assuring that if the positive control had been the target bioentity, it would have been detected. Note that it is only upon analysis of the results that the positive control is "separated" from the target substance.

The term "fixed" as used herein refers to the practice of adding a chemical compound for preserving cell structure for analysis. Traditional fixing agents include, but are not limited to, paraformaldehyde, glutaraldehyde, methanol, or other alcohols. Although a fixed cell remains physically stable for an extended period, some cellular antigens may not be preserved, which is detrimental to any process (staining, separation, labeling, etc.) which requires antigen integrity.

The term "stabilized" is used herein to signify a fixed cell that maintains antigen integrity in a reproducible manner over time. Therefore, a stabilized cell can be successfully and reproducibly stained, separated, or labeled in an antigen-specific reaction.

The preferred magnetic particles or ferrofluids for use in carrying out this invention are particles that behave as colloids. Such particles are characterized by their submicron particle size, which is generally less than about 200 nanometers (nm), and their resistance to gravitational separation from solution for extended periods of time. In addition to the many other advantages, this size range makes them essentially invisible to optical analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by coating molecules which are bonded, e.g., physically absorbed or covalently attached, to the magnetic core and which confer stabilizing colloidal properties. The coating material should preferably be applied in an amount effective to prevent non-specific interactions between biological macromolecules found in the sample and the magnetic cores. Such biological macromolecules may include sialic acid residues on the surface of non-target cells, lectins, glycoproteins and other membrane components. In addition, the coating material should contain as high a magnetic mass/nanoparticle ratio as possible. The size of the magnetic crystals comprising the core is sufficiently small that they do not contain a complete magnetic domain. The size of the nanoparticles is such that their Brownian energy exceeds their magnetic moment. Consequently, North Pole-South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. No. 5,698,271. In a preferred embodiment of the invention, magnetic particles coated with anti-EpCAM antibody are prepared as described in U.S. Pat. No. 6,365,362. Magnetic particles coated with anti-epithelial antibodies sold by other companies, including Miltenyi Biotec and Dynal can also be used in these rare cell isolation procedures.

The following table shows exemplary cell lines that can be used as a source of control cells. Each of these cell lines expresses surface markers that are specific to the disease, making them useful candidates for control cells.

| Cell line | Marker | Tumor origin |
| --- | --- | --- |
| SKBR3 | Mammoglobulin | Breast |
|  | Human milk fat globulin |  |
|  | Her2neu |  |
| MCF-7 | Estrogen receptor | Breast |
| LNCaP | PSMA | Prostate |
|  | PSA |  |
|  | Androgen receptor |  |
| CEM | CD4 | T cell leukemia |
| Raji | CD19 | B cell leukemia |
| SU-DHL | CD20 | B-NHL |
| C32 | CD146 | Melanoma |

Other tumor cell lines may be used as a source of control cells provided they have surface markers and the capability of accepting additional labels. There are similar cell lines for colon and bladder cancers, as well as additional cell lines for breast and prostate cancers.

The rare cell assay, as applied to the determination of circulating tumor cells, involves the selection and detection of cancer cells present in blood. Tumor cells in patients with epithelial derived tumors can be present in frequencies below one cell per ml of blood. That is why it is preferred to process 5-10 ml of blood per assay. An exemplary assay of the invention consists of several steps:

1) Incubation of blood with magnetic particles attached to an antibody that is specific for epithelial cells, in order to label epithelial tumor cells in blood;
2) Separation of magnetically labeled cells from unlabeled cells by magnetic separation, followed by a wash step to remove any carry-over leukocytes;
3) Further selection of epithelial cells by labeling with an antibody specific for epithelial cells conjugated to a fluorochrome; and
4) Analysis of cells by different optical platforms to ascertain cell numbers and types.

Two types of controls may be used. One control is external, in which known number of epithelial tumor cells are added to a normal control blood sample, which is then assayed along with the patient sample. The external control assay allows one to determine the recovery of spiked tumor cells, which should fall within set specifications. It may be difficult to utilize such an assay because the laboratory may not have cells to spike into blood, or may not be able to obtain a normal sample of 5-10 ml blood. In the manual steps of the assay method, external controls may not be ideal, as they do not control random operator errors with respect to addition of reagents and skipping of any reagent(s). In such cases, the best control will be internal, where the number of epithelial cells spiked into a patient sample can be recovered and detected.

In order to differentiate a large number of spiked control cells from a smaller number of actual tumor cells present in the patient blood, the spiked control cells must be pre-labeled with a specific fluorescent dye or other marker with the high labeling efficiency (fewer than one unlabeled cell in $10^5$). More than one type of label may be used to further ensure that no unlabeled control cells are present. However, such redundant labeling is not normally needed. The presence of this specific label on cells during analysis will indicate a control cell. To utilize such a test, it is necessary to provide positive labeled controls along with the assay. Cultured tumor cells with the appropriate markers can be used as positive controls but they are not stable for more than 24 hours. Therefore, the positive labeled control cells should be pre-labeled and stabilized for long-term use. The specific antigens present on positive controls must also be preserved during the pre-labeling and remain preserved under suitable storage conditions.

The number of control cells recovered at the end of the procedure conveys certain information to the analyst. It ensures that the test was performed correctly and that the reagents and systems were working properly. The recovery of tumor cells from whole blood, as described in U.S. Pat. No. 6,365,362, does not describe the use of control cells. In artificially created biological samples using cultured tumor cells in blood for example, cultured spiked control cells, recoveries of the spiked cells range from 60-95%. Cells may be lost at numerous steps in the procedure, including separation, washing, resuspension, and transferring of the sample into the analysis platform, as well as the efficiency of the analysis platform. When a flow cytometer is used as the analysis platform, a small amount of liquid is often left at the bottom of the sample tube, which results in a large component of the error. Those skilled in the art of flow cytometry generally account for this non-reproducible, constant source of error in their analyses by using an independent source of events to compare to their counts.

Unfortunately, in a biological system, one can never assume that two different cells will behave identically. Therefore, in a rare cell isolation procedure, one cannot assume that the target cells and control cells are recovered at an identical rate. However, one can show that patient tumor cells and cultured breast cancer cells share many pertinent characteristics, behave in a similar manner, and can be used to accurately reflect recovery. It is important to note, that it is not to be implied from the description of this invention provided herein that control cells and circulating epithelial cells are recovered in identical proportions, merely that they are recovered in the same range. As described in U.S. Pat. No. 6,623,982, which is incorporated by reference herein in its entirety, the range of density of the EpCAM antigen, which is used for magnetic collection, is similar in patient samples and in cultured cell lines. There are many cancer cell lines available to the analyst, including lines Colo204, SKBR-3, MCF-7, BT474, and PC3. These cell lines express varying degrees of the EpCAM antigen, but as shown in FIG. 3, the antigen densities of the cell lines reflect the antigen densities of the tumor cells actually found in breast cancer patients. Furthermore, as shown in U.S. Pat. No. 6,623,982 and Example 5 in this specification, cell recovery after magnetic separation of low antigen density cells (the PC3 line) is significantly less than the high antigen density cells (the SKBR-3 line). However, use of the controlled aggregation technique taught in U.S. Pat. No. 6,623,982 brings the recovery of the two cell lines into the same range, compensating for the low antigen density. The control cells described in some of the examples of the present application are modified cells chosen from among these cell lines. The control cells' antigen densities also fall in the range of antigen densities reported in actual breast cancer patients. Additionally, the controlled aggregation technique described in U.S. Pat. No. 6,623,982 is used to bring recovery of low antigen density tumor cells up into the same range as the cells with the higher antigen density. Thus, the recovery of control cells and patient tumor cells should be comparable, even if the tumor cells in the patient have a low level of antigen density.

If the density of the target cell is suspected to be outside the predetermined antigen density and the aggregation technique described in U.S. Pat. No. 6,623,982 is not available, the problem can be circumvented with the use of two separate populations of control cells, one set having a low antigen density and another having a high antigen density. Whether an internal or external control is preferred, analysis of the target cells will be based upon a low to high range of antigen densities as defined by the selected control sets.

In light of this discussion, it is tempting to assume that if 1000 control cells were added to 10 ml of whole blood from a cancer patient and 800 control cells and 8 tumor cells were recovered, therefore there were 10 tumor cells in the original 10 ml blood sample. However, as has just been acknowledged the recovery of control cells and the recovery of tumor cells are similar, not identical. Additionally, when dealing with rare events, such proportional calculations are not warranted. It is more accurate to conclude that 8 tumor cells were recovered from a starting volume of 10 ml in a test that also recovered 80% of the control cells. Of course, this result assumes that the control cells were recovered in the appropriate region of the flow cytometry histogram or with the appropriate fluorescent characteristics, if a different optical platform is used.

An advantage of the control cells and methods of use thereof of the present invention is that if a reasonable or anticipated number of control cells are recovered with the appropriate fluorescent characteristics, it cannot be disputed that when epithelial cells are recovered from a patient blood sample, they are anything but epithelial cells. Except for a few obscure diseases or cored epidermal cells from needle punctures, sources of circulating epithelial cells are those released from tumors. The design of the antibodies used effectively eliminates non-specific binding, to such an extent that tumor cell counts in the single digits can be seen amongst the $5-10 \times 10^7$ leukocytes in a 10 ml blood sample. However, accuracy of this test can be enhanced via the use of a control to confirm that the reagents and the process are working correctly. The appearance of a large number of appropriately located control cells, acting as an internal positive control validates the test method and results.

The following examples further describe in some detail the process of using the control cells of this invention. Several preferred embodiments for practicing the methods of the invention are also set forth. These examples are intended to illustrate, rather than limit the invention. Although these examples show the effective use of control cells in the selection of circulating tumor cells, it should be evident to one skilled in the art that with the proper choice of antibodies, cell lines, and magnetic particles, the teaching of the instant invention can be extended to the selection of other rare cells from other biological specimens.

EXAMPLE 1

Preparation of Stabilized Pre-Labeled Control Cells

The positive control cells can be pre-labeled with diverse markers. One method entails labeling cells using a lipophilic, membrane-specific fluorescent dye. There are numerous types of membrane dyes known in the art which are available commercially. Carbocyanines are among the most strongly absorbing membrane dyes known. Membrane dyes label cells by binding to membrane lipids. It is important that this labeling does not prevent the antibody binding to specific epithelial antigens. The binding of the dye to cells should be essentially non-reversible, and no leakage should occur during storage and test procedures. Another approach is to label cells using a fluorescent-antibody conjugate specific for cell surface antigens. A further approach entails labeling cellular components with fluorescent dyes. Examples of this approach include, without limitation, DAPI and Hoechst 33342 for double stranded DNA, acridine orange for DNA and RNA, various rhodamine derivatives for mitochondria and the endoplasmic reticulum, neutral red for lysosomes, or lipophilic BODIPY for golgi apparatus. In the present example, labeling cells with a lipophilic fluorescent membrane dye is described.

Cultured cells derived from breast cancer were used in this example. The SKBR-3 cells that were adhered to the flask were released with trypsin and were washed once with phosphate buffered saline (PBS) by centrifugation. The cells were washed a second time with Diluent C (Sigma, cat. #CGL-DEL). The cells were then resuspended in Diluent C and the cell concentration was adjusted to $1 \times 10^6$ cells/ml. A fluorescent, 3,3'-dihexadecycloxacarbocyanine perchlorate ($DiOC_{16}(3)$) membrane specific dye was selected to label cells. $DiOC_{16}(3)$ was purchased from Molecular Probes (catalog number D-1125). The dye has maximum fluorescence emission at 501 nm. A stock solution of 50 μM $DiOC_{16}(3)$ was prepared in 5% mannitol with 1% dimethyl sulfoxide. The washed cells were mixed with $DiOC_{16}(3)$ solution at 1:1. Then the tube was tightly covered in aluminum foil, and the labeling was allowed to proceed at room temperature for 30 minutes with occasional mixing. The sample was centrifuged at 2,000 rpm for 5 minutes to remove unreacted dye from the cells. The supernatant was aspirated and cell pellet was resuspended in PBS. The cells were washed again by centrifugation. The cell pellet was resuspended in permeabilizing solution (Immunicon part No. 6025) and adjusted to a cell concentration of $1 \times 10^6$/ml. The permeabilization step enables binding of intracellular antigens by antigen-specific antibodies. The cells were incubated with permeabilizing solution for 15 minutes at room temperature.

After the permeabilization step, the cells were fixed to enhance stability. The cells were then centrifuged to remove excess permeabilizing solution. The cell pellet was resuspended in PBS and washed/centrifuged once more. Finally, the cells were again resuspended in PBS at a cell concentration to $1 \times 10^6$ cells/ml. Paraformaldehyde (PFA) was added the cell suspension at a final concentration of 0.5%. The tube was covered with aluminum foil and the cells were incubated while mixing at room temperature for 2 hours. After 2 hours, the excess PFA was removed by centrifugation. The cell pellet was resuspended in PBS and washed twice by centrifugation. After the second wash, the cell pellet was resuspended in PBS and cell concentration was adjusted to about $1.0$-$2.0 \times 10^5$ cells/ml. The cells were stored in the dark at 4° C. Cells $DiOC_{18}(5)$ and other markers using similar protocols. Protocols suitable for staining adherent cells, as known in the art, may also be used.

Control sets are prepared by staining separate populations of identical cells with two dyes exhibiting different spectral characteristics at similar or different staining intensities thereby allowing ratiometric monitoring of assay performance. Populations based upon cell type, surface antigen density, or cell size can be similarly separated into different spectral sets.

The preferred dyes for preparing controls are fluorescent lipophilic dyes with a high affinity for lipophilic cell membrane components. The requirements for such dyes are: suitable excitation/emission spectra to minimize interference with detection dyes of the target cells, efficient and uniform staining of all cells, substantially irreversible binding to the cell membrane, minimal leakage and transfer of dye during storage, optical stability to photobleaching both during long-term storage and intense irradiation by laser light. Membrane dyes that largely meet these requirements are exemplified collectively as long-chain lipophilic carbocyanines, indocarbocyanines and indodicarbocyanines designated by the abbreviations DiOC12(3), DiOC12(5), DiOC12(7), DiOC14(3), DiOC14(5), DiOC14(7), DiOC16(3), DiOC16(5), DiOC16(7), DiOC18(3), DiOC18(5), DiOC18(7) for carbocyanines and the corresponding carboindocyanines (DiI) and carboindodicyanines.(DiD) analogs and derivatives thereof. Such redundant labeling optionally can be done by concurrent or sequential addition of the second pre-labeling dye, and either before or after fixation of control cells. The more soluble disulfonated (DS) and sulfopropyl (SP) derivatives, exemplified by DiIC18(5)-DS and SP-DiOC18(3) can also be used as membrane stains. Also suitable are lipophilic aminostyryl dyes, designated as DiA dyes, e.g. 4-Di-16-ASP. In general, long chain analogs of numerous fluorescent dyes, e.g. C18 rhodamine B and C18-fluorescein also have high membrane affinities. Stains for other cellular organelles also are available and applicable. Most of these dyes are available from Molecular Probes, Inc., Eugene, Oreg., or can be synthesized by published methods (F. M. Hamer, The Cyanine Dyes and Related Compounds, Interscience, 1964).

Control cells also can be made by labeling cell surface antigens with fluorescent antibodies having an affinity for such antigens as exemplified by the preparation of control SKBR cells labeled with fluorescent HER81 antibody. Labeling two different cellular components also allows facile dual labeling of individual control cells with two structurally and spectrally different fluorophores. Redundant pre-labeling of the same,or different structural cellular elements gives rise to a control cell that further reduce the already low probability of misclassifying a control cell as a tumor cell. For example when single labeling of an individual control cell, a probability exists that less than 1 in 1000 will not be detectably labeled. Redundantly labeling of an individual control cell reduces the failure in labeling probability to less than 1 in 1 million cells.

FIG. 1 shows flow cytometric analysis of 5,000 control cells in 500 μl PBS. A threshold was set on forward light scatter and the cells were gated on forward and right angle scattering. FIG. 1a shows the histogram of the fluorescence intensity in FL1 ($\lambda = 530 \pm 30$ nm). FIG. 1b shows the histogram of the fluorescence intensity in FL2 ($\lambda = 585 \pm 42$ nm).

FIG. 1c shows the histogram of the fluorescence intensity in FL3 (λ=670+nm). As can be seen in the histograms, all cells stained homogeneously.

EXAMPLE 2

Preparation of Pre-Labeled Control Cells Using an Antibody Conjugated to a Fluorescent Dye In this example, the SKBR-3 cultured tumor cells described in Example 1 were again used. However, the cells were pre-labeled with a Her2neu antibody conjugated to a cyanine dye. Anti-Her2neu specifically binds a surface antigen present on certain tumor cells including SKBR-3. The Her2neu MAb was conjugated to a Cy2™ dye using a N-hydroxysuccinimide ester of Cy2™ dye (Amersham catalog # PA22000) and following the manufacturer's recommendations.

SKBR-3 cells, adhered to the flask, were released with trypsin and washed twice with PBS by centrifugation. The cells were resuspended in permeabilization solution and stained with Her2neu-Cy2® dye for labeling. Permeabilization reagent did not have any effect on staining of cells with antibody. The final concentration of antibody during staining was 2 µg/ml and the concentration of cells was $1 \times 10^6$ cells/ml. The staining and permeabilization were done in the dark by covering the tube with aluminum foil for 15 minutes. After permeabilization and staining, the cells were fixed for stabilization as follows.

The cells were centrifuged to remove excess permeabilizing solution and unreacted antibody. The cell pellet was resuspended and washed once more with PBS. The cells were again resuspended in PBS and cell concentration was adjusted to $1 \times 10^6$ cells/ml. Five percent PFA was added to cells, resulting in a final PFA concentration of 0.5%. The cells were incubated in a tube covered with aluminum foil at room temperature for 2 hours with constant mixing. After two hours, the sample was divided into two tubes. One tube was stored in the dark at 4° C. without removing the excess PFA. The excess PFA was removed from the second tube by centrifugation. The cell pellet was resuspended in PBS and washed twice by centrifugation. After the second wash, the cell pellet was resuspended in PBS, and the cell concentration was adjusted to about $1.0-2.0 \times 10^5$ cells/ml. The final cell suspension was stored in the dark at 4° C.

EXAMPLE 3

Stability of Pre-Labeled Control Cells

Fresh cells are generally stable for only one or two days. After this time, the antigens begin to shed and soon the cells disintegrated, causing cell number to decrease drastically. The pre-labeled control cells described in Examples 1 and 2 remained stablity for much longer periods. Two important criteria were used to follow stability: physical stability and biological stability. Physical stability is defined as the presence of an intact cell in a suspension. Biological stability is defined as the preservation of antigens present on cell surfaces and inside cells. Both physical and biological stability are important indicators of functional stability of control cells.

The physical stability of control cells was observed as a function of time by determining the number of cells present in suspension using flow cytometry for cell size, presence of a nucleus, and integrity of antigens. Two antigens were checked for integrity, which are important in the instant invention for use as control cells. The first antigen was EpCAM, which is used to capture cells. The second antigen was cytokeratin, which is used for detection. Spiking a known number of cells into normal blood provided the antigen stability data by recovery and subsequent detection using EpCAM-ferrofluid/anti-cytokeratin-fluorochrome. In this example, the stability of control cells prepared in Example 2 was examined.

Physical Stability: Cell Number

Cells prepared as described in Example 2 were stored undisturbed in the dark at 4° C. One set of control cells was fixed with PFA, with the excess PFA removed after 2 hours. The other set of cells was identical, except that the PFA was not removed after fixing. In both cases, a stored stock was diluted and the cell number was determined as described below. All cell counts were determined in triplicate.

Two hundred microliters of permeabilization solution was added to a 12×75 mm polystyrene tube. The cell stock was mixed by vortexing and 20 µl of cells were added to the permeabilization solution tube. Then 5 µl of anti-cytokeratin conjugated to PE was added to the cells to stain the cytokeratin antigen. The cells were mixed and incubated at room temperature for 15 minutes. Three hundred microliters of PBS were added to each sample and mixed. Ten microliters of ProCOUNT nucleic acid dye (Becton Dickinson Immunocytometry Systems (BDIS), San Jose, Calif.) were added to sample to stain the DNA present in cells and 10,000 (10 µl) of fluorescent beads (Beckman-Coulter, catalog No. 6607007) were added. The sample was then analyzed by FACSCaliber flow cytometer using FL1 as threshold. The fraction of the fluorescent beads acquired in the flow cytometer was used to determine the amount of sample analyzed by flow cytometry, which in turn was used to calculate the number of control cells present in the sample. This study was followed as a function of time. The results are shown in Table 1a.

TABLE 1a

| Days | Cells stored in the presence of excess PFA ($10^5$ cells/ml) | Cells stored in the absence of excess PFA ($10^5$ cells/ml) |
|---|---|---|
| 1 | 1.5 ± 0.01 | 1.3 ± 0.2 |
| 15 | 1.3 ± 0.04 | 1.2 ± 0.1 |
| 30 | 1.3 ± 0.1 | 1.3 ± 0.04 |
| 60 | 1.5 ± 0.1 | 1.5 ± 0.1 |
| 90 | 1.4 ± 0.01 | 1.1 ± 0.1 |
| 120 | 1.7 ± 0.2 | 1.5 ± 0.04 |
| 180 | 1.7 ± 0.1 | 1.4 ± 0.1 |
| 270 | 1.9 ± 0.1 | 2.1 ± 0.1 |

Biological Stability: Recovery of Spiked Control Cells from Blood

A known number of control cells (as determined above), PFA containing stored cells, or fresh cells in cell buffer were spiked into 1 ml of plasma-depleted blood in a 12×75 mm tube. Plasma-depleted blood was prepared by centrifuging blood to separate blood cells from plasma. After centrifugation, most of the plasma was removed by aspiration. Subsequently, 0.5 ml of wash-dilution buffer (Immunicon catalog No. B2110) was added to the pellet. After mixing the sample, 20 µl of EpCAM ferrofluid was added to the blood sample and mixed well. The tube was placed in a magnetic separator (Immunicon catalog No. QS-012) for 10 minutes. The tube was taken out of the magnet and the sample mixed by vortexing and placed back in the magnetic separator for 10 minutes to collect the magnetically labeled cells. The uncollected sample was aspirated and the tube was removed from the magnetic separator. The magnetically collected cells were resuspended in 0.75 ml of wash-dilution buffer and re-separated in a magnetic separator for 10 minutes. The uncollected sample was discarded and the collected cells were resuspended in 200 µl of permeabilization solution after removal of the tube from the magnetic separator.

The sample was then stained with labeled antibodies to determine the recovery of tumor cells by flow cytometry as follows. Five microliters of PE-conjugated Mab, which is specific for cytokeratin and is present in control cells, was added to the sample and incubated for 15 minutes. After incubation, 1 ml of wash-dilution buffer was added to the tube and a magnetic separation was performed for 10 minutes in order to remove excess staining antibodies. The magnetically collected cells were resuspended in 500 µl of wash-dilution buffer. Then 10 µl of ProCOUNT nucleic acid dye and 10,000 (10 µl) of fluorescent beads (Beckman-Coulter, catalog No. 6607007) were added. The sample was then analyzed on a FACSCalibur flow cytometer using FL1 as threshold. The fraction of the fluorescent beads acquired in the flow cytometer was used to determine the amount of sample analyzed by flow cytometry that was then used to calculate the recovery of spiked control cells. The percentage recoveries of control cells are given in the Table 1b.

TABLE 1b

| | Recovery of spiked cells (%) | | |
|---|---|---|---|
| Days | Fresh cells | Control cells (stored in the presence of excess PFA) | Control cells (stored in the absence of excess PFA) |
| 1 | 72 ± 5 | 64 ± 6 | 82 ± 10 |
| 15 | 88 ± 5 | 74 ± 0.0 | 76 ± 4 |
| 30 | 97 ± 1 | 67 ± 1 | 93 ± 1 |
| 60 | 82 ± 4 | 48 ± 0.1 | 72 ± 6 |
| 90 | 86 ± 2 | 33 ± 0.0 | 64 ± 6 |
| 120 | 70 ± 2 | 34 ± 9 | 80 ± 1 |
| 180 | 88 ± 5 | 39 ± 0.0 | 69 ± 4 |
| 270 | 80 ± 4 | 35 ± 8 | 73 ± 1 |

Table 1a shows the physical stability of cells. There is no significant change in cell concentration up to 270 days (9 months) in the presence or absence of excess PFA. Changes in cell concentration from one time point to another are due to within experimental errors. There is no trend over the 270 day period. These data show that cell stability physically can be maintained by treating cells with PFA and storing them with or without excess PFA.

Table 1b shows the recovery of control cells as a function of time. These data are graphed in FIG. 2 and show the biological stability of control cells. The antigens present on and in the cell should be preserved for selection from blood cells and detection. The EpCAM present on the surface of control cells is used for selection of cells, which is achieved by conjugating anti-EpCAM MAb to magnetic particles. The binding and selection of control cells by anti-EpCAM magnetic particles is directly related to presence and reservation of EpCAM antigen on cells. The recovery of control cells will decrease if the EpCAM antigen is not preserved, as magnetic particles will not bind control cells. The control cells after selection were detected by using anti-cytokeratin conjugated to a fluorochrome. The cytokeratin antigen is present only in control cells and not in blood cells. The magnetically selected control cells will not be detected if the cytokeratin antigen is not preserved, and the recovery of control cells will be lower. The preservation of both EpCAM and cytokeratin antigens are essential for recovery of control cells.

The recovery of control cells was compared with fresh cells at each time point. Fresh cells were prepared on the day they were tested. As seen in Table 1b, there was no significant change in recovery of fresh cells and control cells stored without excess PFA as a function of time. The recovery of control cells that were stored in the presence of excess PFA tended to decrease significantly as compared to fresh cells. This shows that the presence of PFA during cell storage damages the antigen by reacting with the exposed active sites. This study shows that exposure of PFA to cells for a limited amount of time will keep cells physically and biologically stable.

EXAMPLE 4

Analysis of EpCAM Antigen Levels on Tumor Cells in Patients with Breast Cancer

In this and the following example, it will be shown that breast cancer cells found in patients have a highly variable EpCAM antigen density that can vary over a 1-3 log range. However, despite this high variability, it is also shown in the following example that the magnetic separation technique employed successfully captures a reproducible percentage of tumor cells, whether or not they have high or low antigen densities. The conclusion that can be drawn from these results is that the recovery of control cells accurately reflects the recovery of circulating tumor cells in patient samples.

Biopsies of eighteen pathologically confirmed breast cancers ranging in size from 0.1-2.5 cm, stored in saline, were finely minced with scissors and then passed through a 53 µm nylon filter (SpectraMesh, SPECTRUM, Houston, Tex.) to remove large cell clumps. Cells were washed in PBS/1% BSA/50 mM EDTA (cell buffer), then resuspended in cell buffer. Total nucleated cell counts were performed by hemacytometer with acridine orange/ethidium bromide.

Approximately 20,000-50,000 total nucleated cells (10-50 µl of cell suspension) were placed in each of eighteen sets of three 12×75 mm tubes. The volume was brought up to 150 µl with cell buffer. All tubes then received 0.25 µg of CD45 PerCP. Tube 1 received no reagent (autofluorescence control), tube 2 received 20 µl FastImmune PE Isotype Control, and tube 3 received 0.25 µg of the EpCAM MAb-PE. Cell suspensions were incubated with reagents for 15 minutes, then 1 ml of cell buffer was added to each tube, and the tubes were centrifuged. Supernatants were carefully removed and cell pellets were resuspended in 500 µl FACS Lysing Solution (BDIS). At this point, 3.0 µg (10 µl at 300 µg/mL) of the ProCOUNT nucleic acid dye and 50 µl of FACSCount Counting Control High beads (BDIS) were added to each tube. Samples were then run on a FACSCalibur (BDIS) with threshold set on FL1 and the voltage of the photomultiplier of FL2 was set such that the autofluorescence signals of the unstained cells were present in the first decade.

The population of cells that stained with the nucleic acid dye and EpCAM, but did not stain with CD45, were considered the tumor cells within the cell suspensions. The mean fluorescence intensity of the EpCAM positive cells was determined for each breast tumor sample. FIG. 3 illustrates the mean fluorescence intensity of each of the tumor cells in each of the 18 breast cancer biopsies. The range of background staining is indicated along the vertical axis with dashed arrows. The ranges found for the mean fluorescence intensity for a variety of tumor cell lines Colo204 (high), SKBR-3, MCF-7, BT474, and PC3 (low) are indicated on the right axis.

EXAMPLE 5

Recovery of Spiked Low and High EpCAM Antigen Density Cells from Blood with and without Aggregation of CA-EpCAM MAb Ferrofluid Breast carcinoma cells (SKBR-3) have about 7-times higher EpCAM antigen density, compared to PC3 cells, and were chosen as the model of high antigen density tumor cells for this example. A known number of SKBR-3 or PC3 cells in cell buffer were spiked into 1 ml of washed blood separately in a 12×75 mm tube. Washed blood was prepared by mixing 10 ml acid citrate dextrose (ACD) anticoagulated blood with 10 ml wash dilution buffer (WDB Immunicon catalog No. B2110), comprised of a phosphate buffer which contains proteins to prevent any nonspecific binding of cells to the reagents. It was then centrifuged 10 minutes at 2000 rpm. The supernatant was aspirated, and the volume was raised up to 20 ml with WDB. It was mixed and centrifuged again. The supernatant was aspirated, and the volume was raised up to 10 ml, resulting in 10 ml "washed blood." Five hundred microliters of WDB and 15 µl of PBS containing aggregation reagent (Streptavidin Immunicon part No. 6026) were added to the sample. After mixing the sample, 25 µl of controlled aggregation epithelial cell adhesion molecule ferrofluid (CA-EpCAM FF, Immunicon part No. 6029) was added and the blood sample mixed well and incubated for 15 minutes. After incubation, the tube was placed in a quadrupole magnetic separator for 10 minutes to collect magnetically labeled cells. The magnetically isolated cells were analyzed for recovery of tumor cells by flow cytometry.

TABLE 2

| concentration of aggregation reagent (µg/ml) | PC3 cells Recovery (%) | SKBR-3 cells Recovery (%) |
| --- | --- | --- |
| 0 | 23 | 91 |
| 2 | 77 | 98 |

The data reveal a significant difference in recovery of tumor cells between low and high antigen density cells when the aggregation reagent was not added to the blood sample. There were also no ferrofluid aggregates in solution or on cell surfaces without aggregation reagent, as observed with microscopy. Addition of the aggregation reagent to the blood sample increased the recovery of low antigen density PC3 cells significantly (3-fold) with a commensurate increase of ferrofluid aggregation in solution and on the cells. On the other hand, there was only a small difference in recovery of high antigen density SKBR-3 cells with and without aggregation reagent present in the blood sample. There was enough ferrofluid on SKBR-3 cells, even without ferrofluid aggregation, to collect them effectively and to provide a high recovery. In the case of low antigen density cells, there was not enough ferrofluid on cells to be collected effectively by magnetic methods. Ferrofluid aggregation by the aggregation reagent increased the amount of ferrofluid on these cells facilitating collection, effectively resulting in higher recovery. It is also noteworthy that aggregation of ferrofluid increased the recovery of low antigen density cells close to that obtained with the high antigen density cells. In other words, there was no significant difference in recoveries of low and high antigen density tumor cells upon addition of ferrofluid aggregator to the blood sample.

EXAMPLE 6

Control Cells in an Actual Patient Sample with Detection Via the Cell Spotter®

Five milliliters of WDB was added to a 5 ml sample of blood from a patient with prostate cancer. After mixing, the blood was centrifuged for 10 minutes at 2000 rpm, with the brake off. The plasma was removed by aspiration and the volume was made up to 10 ml with WDB. The sample was again mixed and centrifuged. The supernatant was removed by aspiration and the volume of the washed blood was increased to 5 ml with WDB. Control cells were prepared using the method described in Example 1 and then spiked into the 5 ml washed blood sample. Twenty microliters of a $5.0 \times 10^3$ cells/ml control cell stock were used, resulting in a spike of 100 control cells. Then 2.5 ml WDB, 50 µl aggregation reagent and 75 µl CA-EpCAM FF was added in that order and mixed, one item at a time. After mixing, the tube was placed in a magnetic cell separator for 10 minutes. Then the tube was removed, inverted, and placed back in the separator for another 10 minutes. The tube was removed again, inverted, and separated for 20 minutes. Then the liquid in the tube was carefully aspirated, being careful not to disturb the cells and magnetic material on the sides of the tube. The tube was removed from the magnetic separator and 3 ml of WDB were added to the tube, which was vortexed to resuspend the material on the side of the tube. Then the tube was reinserted into the magnetic separator for 10 minutes. The liquid was removed by aspiration while the tube remained in the magnetic separator. The tube was removed from the magnetic separator and the following reagents were added: 200 µl Permeabilization Reagent (Immunicon part No. 6032), 20 µl CD45 FITC (Becton Dickinson catalog No. 347643), 10 µl DAPI (100 µg/ml, Molecular Probes catalog No. D-3571), 15 µl α-Cytokeratin-Cy3® (50 µg/ml), and 5 µl α-Her2neu-Cy5® (50 µg/ml). Note that both Cy3® and Cy5® are conjugated to antibodies following procedures recommended by the manufacturer (Amersham). The sample was vortexed to resuspend the magnetically collected cells, and then incubated for 15 minutes. Then 10 ml of cell buffer (Immunicon part No. 6013) was added and mixed by inversion. After centrifugation (1300 rpm, 10 min, brake off) the liquid was aspirated down to approximately 200 µl and 20 µl 5% paraformaldehyde was added. The entire sample was pipetted into a Cell Spotter® chamber and images were acquired using filter sets for DAPI, FITC, Cy3® and Cy5®.

Figure 4:
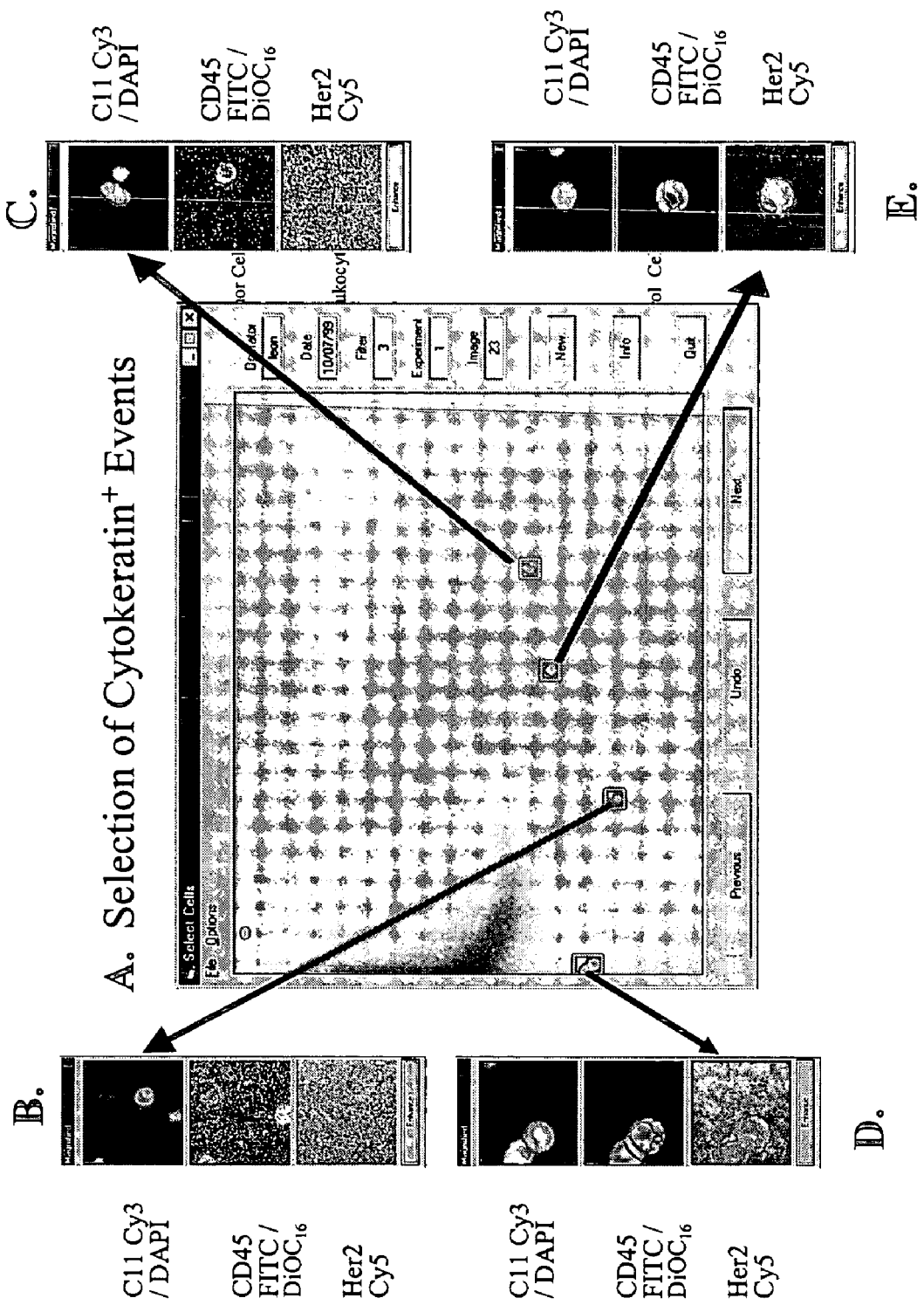

Results of the cell spotting are shown in FIG. 4, panels A-E. FIG. 4A shows one of the Cy3® images. Four boxes are drawn around cytokeratin Cy3+objects with cell-like features. Arrows are drawn from each of these boxes to panels B, C, D and E. In the top image of each of these panels an overlay is shown from the α-Cytokeratin-Cy3® image and the DAPI image; the middle image is the filter in which CD45-FITC and $DiOC_{16}(3)$ staining can be seen; and in the bottom image the staining of Her2Cy5®. The boxes of which the images are shown in panels D and E contain cells that have a nucleus, stain brightly in the FITC filter ($DiOC_{16}(3)$++) and stain positive for Her2neu-Cy5®. Both of these cells are control cells and confirm that the reagents in the test are functional. In this case, 58 of the control cells were identified which indicated that no errors were made in the sample preparation. The other two boxes shown in Panels B and C contain cells that have a nucleus, do not appear in the FITC filter, and do not appear in the Cy5® filter. These cells do have the properties specified for tumor cells that do not express Her2neu. In the boxes are also other cells as can be seen by the presence of a nucleus, these cells however stain with CD45-FITC and are leukocytes. Leukocytes non-specifically binding to α-Cytokeratin-Cy3® will stain with CD45-FITC and can be excluded. Tumor cells non-specifically binding to CD45 can only be discriminated if the cellular properties are distinct from those of leukocytes, in which case they can be earmarked as suspicious. Normal epithelial cells can be discriminated from epithelial cells with malignant features based upon their morphological features as assessed by the nuclear stain (DAPI) and cytoplasmic stain (cytokeratin).

EXAMPLE 7

Internal Control Cells for the Circulating Tumor Cell Assay Analyzed by Flow Cytometry Cells of the breast cancer cell line SKBR-3 are fixed and fluorescently labeled with the compound $DiOC_{16}(3)$. This compound stains cell membranes and can be excited with the argon ion laser line (488 nm) commonly used in flow cytometers. The emission of the dye is detected by the same photomultiplier as is used to detect the fluorescence signals emitted by FITC. The $DiOC_{16}(3)$ stained cells were stored at a concentration of 50,000 cells/ml. In the experiment described here 100 µl of control cells (5000 cells) were added to two 2 ml ACD anticoagulated blood in a 12×75 mm polystyrene tube. To one of these samples 100 µl of unlabeled cells of the breast cancer cell line SKBR-3 was added containing approximately 5000 cells. 2 ml of buffer was added to the blood, carefully mixed and centrifuged at 800 rpm for 10 minutes. Then 2.5 ml of the plasma-buffer mixture was aspirated and discarded. The sample was mixed and 1.5 ml of buffer, 9 µg of Aggregation Reagent and 9 µg of CA-EpCAM FF were added in that order to the sample and mixed, one at a time. Then the tube was placed in a magnetic separator. After 10 minutes, the sample was taken out of the separator, mixed, and placed back in the separator for another 10 minutes. The sample was again taken out the separator, mixed, and placed back in the separator for 20 minutes. The supernatant was removed by careful aspiration and discarded and 1 ml of buffer was added to the tube. The sample was taken out of the separator, ensuring that all of the cells and ferrofluid attached to the wall of the tube were resuspended. The sample was placed back in the separator. After 10 minutes the buffer was aspirated and discarded. The tube was taken out of the separator followed by the addition of 200 µl of a solution permeabilizing the cell membrane, 10 µl of PE labeled monoclonal antibody directed against cytokeratin and 20 µl of FITC labeled antibody. The sample was mixed again assuring that all the ferrofluid and cells attached to the wall were resuspended. 15 minutes after incubation, 2 ml of buffer was added, mixed and the sample was placed back in the separator for 10 minutes. After the buffer was aspirated and discarded, the sample was taken out of the separator and 0.5 ml of Disaggregation Reagent (Immunicon part No. 6027) was added. The samples were then analyzed by flow cytometry.

The instrument settings of the flow cytometer were set using a threshold on the forward light scatter. This setting permits the elimination of non-desired events including ferrofluid particles (170 nm) and residual fluorescently labeled antibodies based on size. In addition, a gate was used eliminating all events that did not stain with FITC or PE such as erythrocytes and platelets. FIG. 5 shows the analysis of both samples. The top two panels (FIGS. 5a-b) show the analysis of the sample that only contained control cells and the bottom two panels (FIGS. 5c-d) show the analysis of the sample that contained both control cells as well as tumor cells. The forward and orthogonal light scattering dot plots are shown to the left (FIGS. 5a, 5c) and the dot plots correlating the FITC versus PE signals to the right (FIGS. 5b and 5d.) Four gates are indicated in the right panels. Gate R3 excludes all negative FITC and PE events. Control cells appear in gate R1, staining brightly with $DiOC_{16}(3)$ (FL1) as well as staining brightly with cytokeratin PE. Leukocytes appear in gate R4, staining with CD45 FITC but not with cytokeratin PE. Tumor cells appear in gate R2, not staining with CD45 FITC or $DiOC_{16}(3)$, but positive for cytokeratin PE. Events that fall outside these regions are considered debris (R3-(R1+R2+R4)). In the top panels 403 leukocytes, 2647 control cells, and 0 tumor cells were detected. As 5000 control cells were added to the original blood sample, 2353 were lost in the procedure. This loss of cells can occur at many steps, such as labeling, separation, aspiration and in this case a major contributor was the fact that approximately 100 µl was left in the tube after data acquisition on the flow cytometer (20% of the sample).

In assay development, it is important to identify the steps that are most critical to the loss of cells. When the assay is used to determine whether or not a patient has cancer cells in the blood and how many cancer cells per volume unit, it is important to know whether or not the sample was accurately processed and whether or not the reagents are functioning properly. In this example, 2674 of 5000 control cells were detected and one can conclude that although the starting blood volume was 2 ml, only 2674/5000×2 ml=1.1 ml was effectively analyzed. As the number of tumor cells detected was 0, one can conclude that in 1.1 ml of blood 0 tumor cells were detected. However, one cannot conclude that in this case 2 ml of blood was analyzed and 0 tumor cells are present. In the case where the control cells would fall in a region below the indicated gate, the reagents failed, and no results can be reported. In the bottom panels, 304 leukocytes, 2667 control cells, and 2129 tumor cells were detected. In this example, 2667 of 5000 control cells were detected and one can conclude that, although the starting blood volume was 2 ml, only 2667/5000×2 ml=1.1 ml was effectively analyzed. As the number of tumor cells detected was 2129, one can conclude that in 1.1 ml of blood 2129 tumor cells were detected (1996 tumor cells/ml of blood).

EXAMPLE 8

Internal Control Cells for the Circulating Tumor Cell Assay that can be Analyzed by Automated Cell Analytical Platforms In this example, a flow cytometer is equipped with a 488 nm argon ion laser as well as a 635 nm laser diode. However, an optical cell analysis instrument, as described in U.S. Pat. No. 5,985,153, equipped with a 535 nm laser diode as well as a 635 nm laser diode could also be used for analysis. The combination of fluorochromes used to label the different probes to identify cancer cells in peripheral blood can be easily changed. In this example, the antibody recognizing the cytokeratin is still labeled with PE, and is excited with the 488 nm laser line or the 535 nm laser diode. The 535 nm light source is closer to the maximum absorption peak of PE, and thus results in a better signal to noise ratio. The antibody recognizing leukocytes is also used to eliminate cells or events that are nonspecifically binding in this configuration. The CD45 antibody is labeled with allophycocyanine (APC) and is excited with the 635 nm laser diode, but not with the 488 nm laser line or the 535 nm laser diode. The advantage of this combination as compared to the FITC/PE combination described in the previous example is that the cross talk of the emission spectra of both fluorochromes does not occur (i.e., no compensation is necessary).

The dye that is used to stain and identify the control cells would be preferably measured in the same channel as the APC channel, provided that the control cells indeed can be separated from the leukocytes as in the previous example. In this example the cells of the breast cancer cell line SKBR-3 are fixed and fluorescently labeled with the lipophilic membrane dye 1,1'-dioctadecyl-3,3,3',3'-tetramethylindodicarbocyanin ($DiIC_{18}(5)$, Fluka.) This compound stains cell membranes and can be excited with the 635 nm laser diode. The emission of the dye is detected by the same photomultiplier as is used to detect the fluorescence signals emitted by APC. The $DiIC_{18}(5)$ stained cells are used at a working concentration of $1\times10^5$ cells/ml. In the experiment described here, 50 μl of control cells (5000 cells) was added to two samples of 2 ml washed blood. To one of these samples, 50 μl of unlabeled cells of the breast cancer cell line SKBR-3 was added containing approximately 5000 cells. The sample was mixed and 1.0 ml of buffer, 9 μg of Aggregation Reagent and 9 μg of CA-EpCAM FF were added to the sample in that order, mixed one at a time, and placed in a magnetic separator. After 10 minutes, the sample was taken out, mixed, and placed back in the separator for another 10 minutes. The sample was again taken out of the separator, mixed, and placed back in the separator for 20 minutes. The tube was taken out of the separator, and 100 μl of a solution permeabilizing the cell membrane, 10 μl of PE labeled monoclonal antibody directed against cytokeratin, and 20 μl of CD45-APC labeled antibody (Pharmingen) were added to the tube. The sample was mixed assuring that all the ferrofluid and cells attached to the wall were resuspended. After incubation for 15 minutes, 1 ml of WDB was added, mixed and the sample placed back in the separator for 10 minutes. After the buffer was aspirated and discarded, the sample was taken out of the separator and 0.5 ml of Disaggregation Reagent was added. The samples were then analyzed by flow cytometry.

Figure 6:
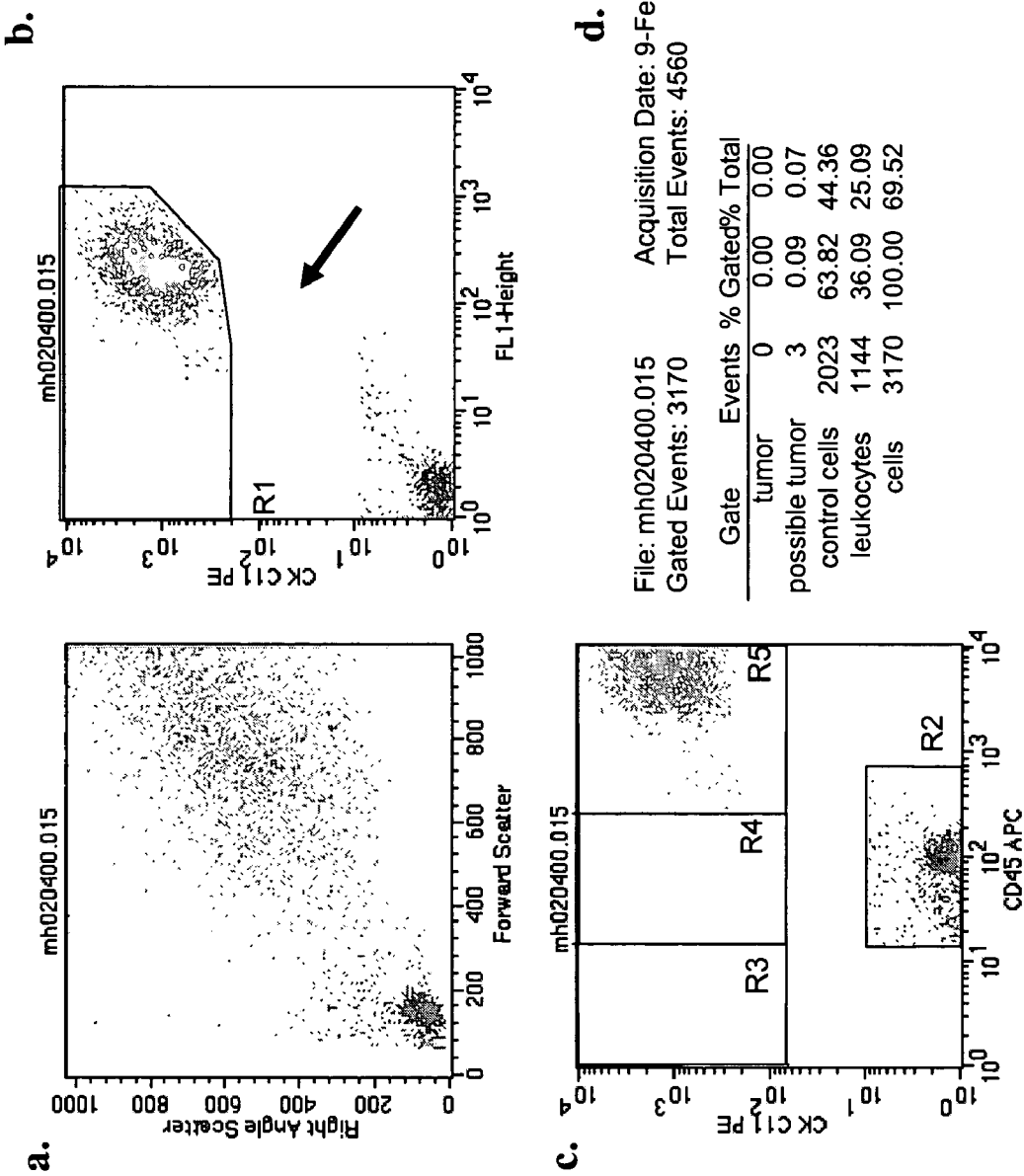
Figure 7:
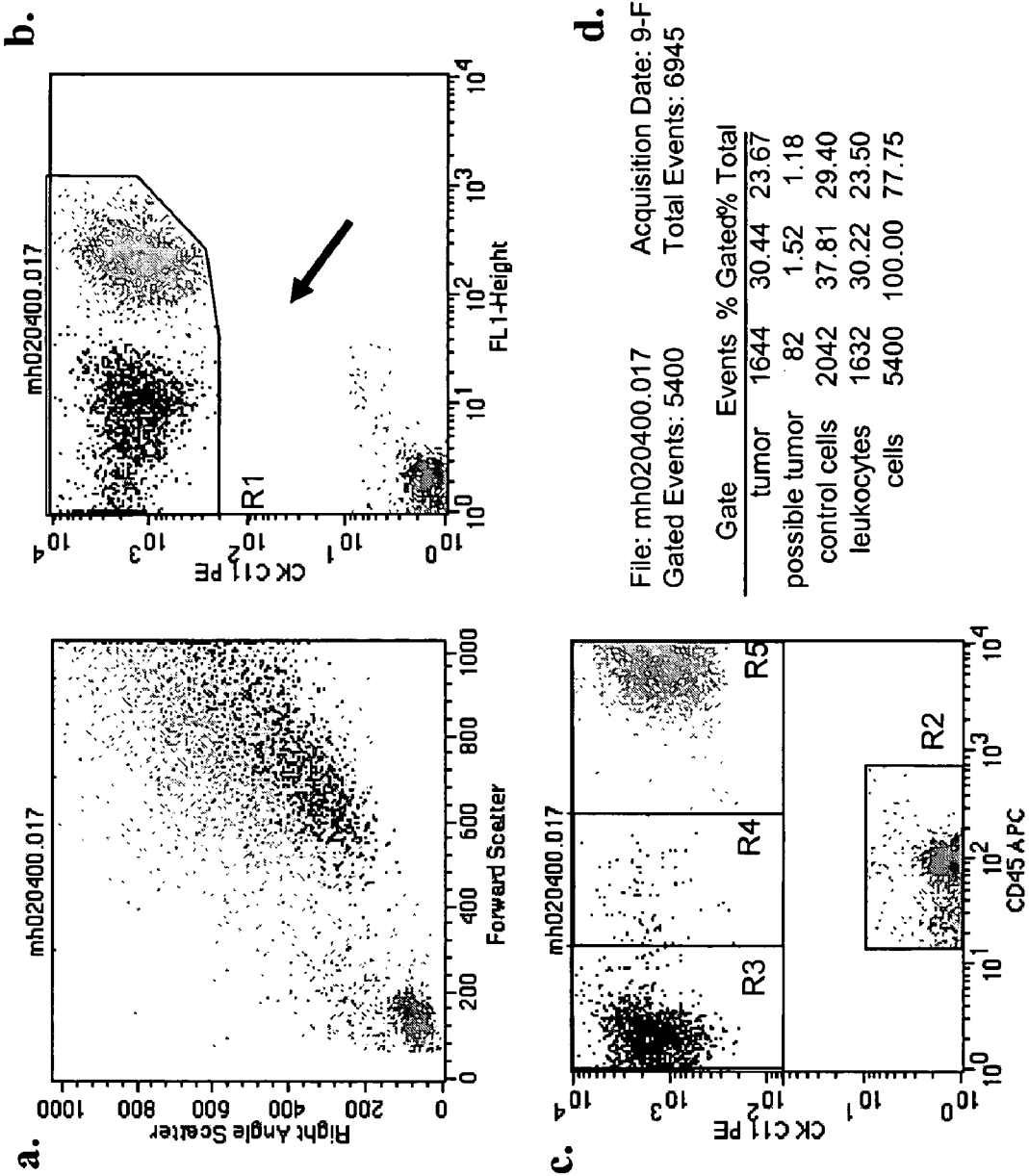

The instrument settings of the flow cytometer were set using a threshold on the forward light scatter. This permits the elimination of non-desired events including ferrofluid particles (170 nm) and residual fluorescently labeled antibodies based on size. In addition, a gate was used eliminating all events that did not stain with APC or PE, such as erythrocytes and platelets. FIGS. 6 and 7 show the analysis of both samples. FIGS. 6a-c show the analysis of the sample that only contained control cells and FIGS. 7a-c show the analysis of the sample that contained both control cells as well as tumor cells. The forward and orthogonal light scattering dot plots are shown in FIGS. 6a and 7a. The dot plots correlating the PE signals versus FL1 (530±30 nm) are shown in FIGS. 6b and 7b. Gate R1 is indicated identifying PE[+] events. The arrow indicates the position of events that are indicative of non-specific fluorescing in the PE and the FL1 channels. The PE versus APC dot plots are shown in FIGS. 6c and 7c. Four gates are indicated. Leukocytes appear in gate R2, staining with CD45 APC, but not with cytokeratin PE. In gate R3, tumor cells appear, not staining with CD45 APC or $DiIC_{18}(5)$, but positive for cytokeratin PE. In gate R5 the control cells appear, staining brightly with $DiIC_{18}(5)$, as well as staining brightly with cytokeratin PE. The cells that appear in gate R4 may be non-specifically bound to CD45-APC, non-specifically binding leukocytes which stain with PE or possible tumor cells. In FIG. 6d, 1144 leukocytes [R2], 2023 control cells [R5], 3 possible tumor cells [R4], and 0 tumor cells [R3] were detected. Possible tumor cells exhibit the fluorescence characteristics of labeled tumor cells, but fall outside the thresholds for tumor cells. These events always lack one feature that would confirm them as actual tumor cells.

As 5000 control cells were added to the original blood sample, 2977 were lost in the procedure. In this example, 2023 of 5000 control cells were detected, and one can conclude that although the starting blood volume was 2 ml only 2023/5000×2 ml=0.8 ml was effectively analyzed. As the number of tumor cells detected was 0, one can conclude that in 0.8 ml of blood 0 tumor cells were detected. One can however not conclude that in the case where 2 ml of blood was analyzed 0 tumor cells were present. In that case, the control cells would fall in a region below the indicated gate, the reagents would have failed, and no results could be reported. In FIG. 7d 1632 leukocytes [R2], 2042 control cells [R5], 82 possible tumor cells [R4] and 1644 tumor cells [R3] were detected. In this example 2042 of 5000 control cells were detected and one can conclude that although the starting blood volume was 2 ml only 2042/5000×2 ml=0.8 ml was effectively analyzed. As the number of tumor cells detected was 1644 one can conclude that in 0.8 ml of blood 1644 tumor cells were detected (2055 tumor cells/ml of blood).

EXAMPLE 9

Storage of Control Cells Under Neutral Buoyant Conditions

Throughout much work with control cells, as with all cells, reproducibility of cellular manipulations is a common problem. Pipetting cells is often irreproducible and depends on effective mixing or suspension of the cells, which immediately begin to settle upon standing. The spiking of tumor cells, the addition of control cells, and the use of fresh cells as controls are all potential sources of error. One novel method of increasing the reproducibility in the use of control cells is to use a neutral buoyant storage system. In this system, the specific gravity of the stabilized control cells would be identical to the density of the storage medium. Thus, the cells would never settle and would remain perpetually mixed.

In this example, different density media were prepared by using bovine serum albumin (BSA) at different concentrations. A 45% BSA solution (Sigma) was diluted to 25%, 15%, 10%, and 5% in PBS. The gradients were prepared in a centrifuge tube as follows: First 3 ml of 25% BSA was added to the empty 15 ml centrifuge tube. Then 3 ml of 15% BSA solution were gently layered on top of the 25% BSA solution without mixing. The 10% BSA solution was gently layered on top of 15%. The 5% BSA solution was gently layered on top of 10%. Different layers of BSA solutions can be seen clearly. Fresh SKBR-3 cultured tumor cells ($2\times10^6$ cells/ml) 1% BSA in PBS, were layered on top of the 5% BSA solution. The 15 ml tube was centrifuged at 400 g for 30 minutes, brake off. After centrifugation, there were major and minor bands visible in the tube. The major band was a wide band of cells on top of 15% BSA solution and the minor band was a much smaller band on top of 10% BSA solution. The minor band contained mostly dead cells. These data show that cultured SKBR-3 tumor cells have a density greater than 10% BSA, but less than or equal to 15% BSA, because the cells did not enter the 15% BSA solution.

To test that SKBR-3 cells will remain in suspension in a 15% BSA solution, the following experiment was designed. SKBR-3 cells ($1\times10^5$) were added to 1 ml of PBS, 15% BSA solution in a 12×75 mm polystyrene tube and mixed well. As a control, $1\times10^5$ SKBR-3 cells were added to 1 ml of PBS, 1% BSA solution in another 12×75 mm polystyrene tube. Both tubes were centrifuged at 400 g for 10 minutes. Centrifugation will bring cells down to the bottom of the tube in regular buffers. There was a cell pellet at the bottom of the 1% BSA in PBS tube. However, there was no cell pellet at the bottom of the tube with 15% BSA because all of the cells remained in suspension. This experiment shows that in a medium where cells and medium have the same density, settling due to gravity will cease. Thus, pipetting from the stock solution will not require re-mixing and will become a reproducible action. Cells stored in such a medium will be superior to cells stored in the traditional manner for other reasons. Clumping or cross-linking will not occur, there will be no sticking to the bottom corner of the vial, and homogeneity of cells will be assured, since anything that damages cells may also change their density. Thus, in the density centrifugation of this method, an additional purification step is introduced.

It will be immediately recognized by those skilled in the art of cell culture that the uses of such a storage system extend far beyond the field of rare cell selection and cancer detection.

EXAMPLE 10

Using Internal Controls at Different Cell Concentrations

Examples 7 and 8 show the use of pre-labeled cells as internal controls at one particular cell concentration. Internal control at one cell concentration will show that the test was done correctly, but does not indicate the efficiency of recovery of cells at different cell concentrations. The number of tumor cells present in patient samples varies and may not be similar to the number of control cells used. However, the recovery of spiked culture tumor cells is linear from 1 cell/ml to 5000 cells/ml of blood in the model study. But, it is not known how the recovery of control cells from patient sample behaves at various concentrations. This can be answered by spiking control cells at different concentrations into the patient sample and recovering them. It can not be achieved by using control cells with same fluorescence intensity for different concentrations. It can be achieved by using different control cells with different intensities of the same fluorescence marker or with different fluorescent markers.

For example, control cells can be prepared with different fluorescence markers, having different characteristic fluorescence properties and can be differentiated easily. In examples 7 and 8, two different types of control cells with fluorescently distinct sets were used. Control cells which were used in example 7 were pre-labeled with DiOC16(3) which has fluorescence emission similar to FITC. In example 8, control cells, which were pre-labeled with DiOC18(5), emit fluorescence similar to APC. FITC emits maximum fluorescence at 519 nm and APC emits maximum fluorescence at 660 nm. These two control cells can be differentiated easily by fluorescence microscopy, flow cytometry, or other optical analytical platforms, including that described in U.S. Pat No. 5,985,153. DiOC16(3) labeled control cells can be used as high concentration (5000 cells/ml blood) control cells and DiOC18(5) labeled control cells can be used as low concentration (5 cells/ml blood) control cells. A known high number and low number of control cells in fluorescently distinct sets are spiked into patient blood and then the recovery of both high and low control cells are determined. The percentage recovery of both cells should be similar if the efficiency of recovery of control cells at low and high cell concentration is the same. The recovery of tumor cells may fall in between low and high control cell concentrations. Then it is possible to calculate the recovery of tumor cells using both low and high control cell recoveries.

Another way of using control cells with various cell concentrations is by spiking control cells having different fluorescence intensities. Control cells with certain fluorescence intensity represent particular cell populations. Control cells with different fluorescence intensities can be prepared by changing the labeling conditions such as the dye concentration or the staining time.

Using the methods of the above examples, the compositions and methods of the invention can be applied to other cell types to produce internal controls for other assays. As new methods for isolation and enrichment of circulating cells are developed, including methods for detecting the many diseases described in U.S. Pat. No. 6,365,362 (incorporated by reference herein), there will be a need for internal controls. By pre-labeling known cell lines that have been shown to behave similarly to the target cells, the above examples demonstrate the possibility to create these controls. Target cells include without limitation circulating cancer cells, such as breast, prostate, colon, lung, kidney, ovarian cancers, leukemia, melanomas, gliomas, and any of the many other cancer types. Each of these has a tumor cell line that could be suitable for producing control cells. Furthermore, other circulating target cells, indicative of disease states such as endothelial cells smooth muscle cells and myocardial cells, can be similarly assayed, and require controls. These cells also have corresponding cell lines, or alternatively, can be cultured and grown to produce functional controls. Finally, assays for infections that result in circulating target cells, such as virally infected cells (HIV), bacteria, and other microbes will require internal controls, which can be provided by the methods of this invention.

EXAMPLE 11

Using External Controls at Different Cell Concentrations

While an internal control would provide the optimum mode for assessing whether the test was done correctly, determination of cell recovery efficiency at different cell concentrations is also appropriate with external controls. While an internal control would provide the optimum mode for assessing whether the test was done correctly, determination of efficiency of cell recovery at different cell concentrations is also appropriate with external controls.

The assay requires controls to cover a clinical range, requiring controls at different concentrations. To do this, the assay needs to be done with multiple samples at different concentrations. But this will be time consuming and not cost effective, especially for large sample volume processors. A more preferred approach is to use one test with different cell concentrations. This can be achieved by pre-labeling cells with spectrally different dyes.

This principle is exemplified in the following where of two different cell concentrations are used as a high and low control. The high and low controls are prelabeled with two distinguishing dyes inorder to differentiate the two sets.

Same cells were used for both controls and labeled with dyes to distinguish between the two sets. The dyes used to label SKBR-3 cells were similar to the example 10. High controls were pre-labeled with DiOC16 (3), which has fluorescence emission similar to FITC. Low controls were pre-labeled with DiOC18(5), which has fluorescence emission similar to APC. FITC emits maximum fluorescence at 519 nm and APC emits maximum fluorescence at 660 nm. These two control cells can be differentiated easily by fluorescence microscopy, flow cytometry, or other optical analytical platforms, including that described in U.S. Pat. No. 5,985,153. After pre-labeling and fixing, both cells were diluted into the final matrix to a final concentration of 350 cells/ml for high controls and 18 cells/ml for low controls. The matrix selected for controls in this example was Histopaque 1083 (Sigma) containing 5% BSA. The viscosity of this matrix was similar to blood with 3.5 ml of each control set used per test.

The controls samples, which contain both high and low controls, were transferred to CellTracks AutoPrep sample tubes. AutoPrep is an automated sample preparation system which enriches CTC from blood using CellSearch reagents for subsequent analysis on CellSpotter or CellTracks. AutoPrep processes the controls similar to the samples and then transfers the final enriched and fluorescence labeled cells (320 ul) to the CellSpotter chambers for analysis on the CellSpotter system. CellSpotter is a semi-automated fluorescent microscope that enumerates fluorescently-labeled CTC's, immunomagnetically captured and aligned. The microscope is equipped with four filters to detect fluorescence images from different dyes. As shown in FIG. 8, high controls are positive in DAPI, PE and Control (FITC) filters. The system automatically counts these cells and reports control cell count. On the other hand, low controls are positive in DAPI, PE and APC filters. The cells will be presented on the browser to the operator to count manually. The operator manually analyzed the images for low controls. The operator clicks the box next to APC box if the object is positive in DAPI, PE and APC filter. The system gives a final report for both control cell number. The profile of the browser images shown are depicted only as an example of the differences in the fluorescence images between high and low control sets. Other possible fluorescent combinations would be appreciated by individuals skilled in the art.

The samples were processed on 3 different days, 3 different AutoPrep instruments and 3 different operators. Each day 8 samples were assayed and the average cell number per day determined. The results are shown in the following table.

| | High Controls | | | | | | | | |
|---|---|---|---|---|---|---|---|---|---|
| | Operator 1/AutoPrep Instrument 1 | | | Operator 2/AutoPrep Instrument 2 | | | Operator 3/AutoPrep Instrument 3 | | |
| | High Control # | S.D. | % CV | High Control # | S.D. | % CV | High Control # | S.D. | % CV |
| Day 1 (N = 8) | 999 | 16.4 | 1.6 | 1018 | 35.3 | 3.5 | 981 | 65.1 | 6.6 |
| Day 2 (N = 8) | 1012 | 29.2 | 2.9 | 994 | 92.6 | 9.3 | 947 | 81.3 | 8.6 |
| Day 3 (N = 8) | 968 | 51.0 | 5.3 | 980 | 39.9 | 4.1 | 976 | 38.5 | 3.9 |
| Average/ Operator (N = 24) | 993 | 38.7 | 3.9 | 997 | 61.1 | 6.1 | 968 | 63.3 | 6.5 |

| | Low Controls: | | | | | | | | |
|---|---|---|---|---|---|---|---|---|---|
| | Operator 1/AutoPrep 1 | | | Operator 2/AutoPrep 2 | | | Operator 3/AutoPrep 3 | | |
| | Low Control # | S.D. | % CV | Low Control # | S.D. | % CV | Low Control # | S.D. | % CV |
| Day 1 (N = 8) | 46 | 9.3 | 20.2 | 49 | 5.5 | 11.2 | 48 | 8.0 | 16.9 |
| Day2 (N = 8) | 47 | 5.6 | 12.1 | 48 | 7.2 | 15.1 | 45 | 7.8 | 17.3 |
| Day3 (N = 8) | 49 | 8.2 | 16.6 | 48 | 6.4 | 13.4 | 43 | 5.0 | 11.6 |
| Average/ Operator (N = 24) | 47 | 7.6 | 16.1 | 48 | 6.2 | 12.8 | 45 | 7.0 | 15.5 |

The above results clearly show that control cells at different concentrations provide a range in the assay. The coefficient of variation (% CV) for high controls was less than 10. The higher %CV for low controls was expected due to lower cell concentration.

While certain of the preferred embodiments of the present invention have been described and specifically exemplified above, it is not intended that the invention be limited to such embodiments. Various modifications may be made thereto without departing from the spirit of the present invention, the full scope of which is delineated in the following claims.

What is claimed is:

1. An improved method for detecting and enumerating rare cells in a mixed cell population by obtaining a blood specimen from a test subject, said specimen comprising a mixed cell population suspected of containing said rare cells, which method comprises preparing an immunomagnetic sample wherein said blood specimen is mixed with magnetic particles coupled to a ligand which reacts specifically with a determinant of said rare cells, to the substantial exclusion of other sample components, contacting said immunomagnetic sample with at least one reagent which labels said determinant of said rare cells, and analyzing said labeled rare cells to determine the presence and number of any said rare cells in said inmiunomagnetic sample, wherein the greater the number of said rare cells present in said sample, the greater the severity of a disease state, and wherein the improvement comprises the addition of two or more fluorescently distinct sets of stabilized cell populations, said fluorescently distinct sets having different concentrations with said sets having different intensities, permeabilized, for use as a range of control cells in said method, and wherein the membranes of said control cells are detectably labeled, and wherein said control cells contain stabilized cellular components and antigenic moieties of said control cells stabilized for a period up to six months by exposure to fixative.

2. The improved method of claim 1, wherein said rare cell is a cancer cell and said disease state is cancer.

3. The improved method of claim 1, wherein said control cells have determinants in common with said rare cells.

4. The improved method of claim 1, wherein said stabilized cell populations are selected from the group consisting of cell number, antigen density, and cell size.

5. The improved method of claim 1, wherein said addition of two or more fluorescently distinct sets of stabilized cell populations are external control cells, wherein said method is an automated process.

6. The improved method of claim 1, wherein said addition of two or more fluorescently distinct sets of stabilized cell populations are internal control cells.

7. The improved method of claim 1, wherein said stabilized cells are redundantly labeled with at lease two distinct fluorescent labels having the same spectral properties.

8. The improved method as claimed in claim 1, wherein said membrane label is selected from the group consisting of long chain lipophilic carbocyanines, long chain lipophilic indocarbocyanines, long chain lipophilic indodicarbocyanines, and analogs thereof, lipophilic aminostyryl dyes, and long chain analogs of C18 rhodamine B and C 18 fluorescein dyes.

9. The improved method as claimed in claim 1, wherein said ligand is an anti-EpCam, and said reagent labels an intracellular cytokeratin, said EpCam and said cytokeratin being present in both said rare cell and said control cell.

10. The improved method as claimed in claim 1, wherein the control cell is an SKBR3 breast cancer cell, further comprising a second detectably labeled surface determinant selected from the group consisting of mammoglobulin, human milk fat globulin, and HER-2/neu.

11. The improved method as claimed in claim 1, wherein the control cell is a MCF-7 breast cancer cell, further comprising a second detectably labeled surface determinant which is an estrogen receptor.

12. The improved method as claimed in claim 1, wherein the control cell is an LNCaP prostate cancer cell, further comprising a second detectably labeled surface determinant selected from the group consisting of PSMA, PSA, and androgen receptor.

13. The improved method as claimed in claim 1, wherein the control cell is a CEM T-cell leukemia cancer cell, further comprising a second detectably labeled surface determinant which is a CD4 molecule.

14. The improved method as claimed in claim 1, wherein the control cell is a C32 melanoma cancer cell, further comprising a second detectably labeled surface determinant which is a CD 146 molecule.

15. An improved kit for screening a patient sample for the presence of circulating tumor cells, said kit having coated magnetic nanop articles with a magnetic core material, a protein base coating material, and an anti-EpCAM coupled, directly or indirectly, to said base coating material, at least one antibody having binding specificity for a cancer cell determinant, and cell specific dye for excluding sample components other than said tumor cells from analysis, wherein the improvement comprises the addition of two distinct sets of stabilized cell populations, said distinct sets having different concentrations with said sets having different intensities, permeabilized, for use as control cells in said kit, said distinct sets of stabilized control cell populations, having determinants in common with said rare cells, wherein said membranes of said control cells are detectably labeled, and cellular components and antigenic moieties of said control cells have been stabilized up to six months, said stabilized control cells being suspended in a buoyant density medium.

16. The improved kit as claimed in claim 15, wherein said stabilized cells are used as an internal control.

17. The improved kit as claimed in claim 15, wherein said stabilized cells are used as an external control for an automated process in the detection and enumeration of rare cells from a mixed population.

18. The improved kit as claimed in claim 15, wherein said buoyant density medium is histopack.

19. The improved kit as claimed in claim 15, wherein the control cell is a SKBR3 breast cancer cell, further comprising a second detectably labeled surface determinant selected from the group consisting of mammoglobulin, human milk fat globulin, and HER-2/neu.

20. The improved kit as claimed in claim 15, wherein the control cell is a MCF-7 breast cancer cell, further comprising a second detectably labeled surface determinant which is an estrogen receptor.

21. The improved kit as claimed in claim 15, wherein the control cell is an LNCaP prostate cancer cell, further comprising a second detectably labeled surface determinant selected from the group consisting of PSMA, PSA, and androgen receptor.

22. The improved kit as claimed in claim 15, wherein the control cells are C32 melanoma cancer cells, further comprising a second detectably labeled surface determinant which is a CD 146 molecule.

* * * * *